US008652179B2

(12) United States Patent
Graham et al.

(10) Patent No.: US 8,652,179 B2
(45) Date of Patent: Feb. 18, 2014

(54) BONE PLATE EXTENDER AND EXTENSION SYSTEM FOR BONE RESTORATION AND METHODS OF USE THEREOF

(75) Inventors: Thomas James Graham, Timonium, MD (US); H. Brent Bamberger, Kettering, OH (US); James Howard Calandruccio, Memphis, TN (US); Thomas A. Wiedrich, Wilmette, IL (US); Louise M. Focht, Del Mar, CA (US)

(73) Assignee: The Cleveland Clinic Foundation, Cleveland, OH (US)

( * ) Notice: Subject to any disclaimer, the term of this patent is extended or adjusted under 35 U.S.C. 154(b) by 1474 days.

(21) Appl. No.: 12/114,619

(22) Filed: May 2, 2008

(65) Prior Publication Data

US 2009/0275987 A1 Nov. 5, 2009

(51) Int. Cl.
*A61B 17/80* (2006.01)

(52) U.S. Cl.
USPC .......................................... 606/280; 606/902

(58) Field of Classification Search
USPC ..................... 606/70–71, 280–286, 902–906
See application file for complete search history.

(56) References Cited

U.S. PATENT DOCUMENTS 565,255 A 8/1896 Belden
583,455 A 6/1897 Bush
1,608,790 A 11/1926 Henslow
2,031,483 A 2/1936 Interrante
2,031,484 A 2/1936 Interrante
3,939,828 A 2/1976 Mohr et al.
4,409,970 A 10/1983 Carrel
4,658,822 A 4/1987 Kees, Jr.
4,838,254 A 6/1989 Gauthier
4,852,559 A 8/1989 Chernoff
5,006,120 A 4/1991 Carter
5,013,314 A 5/1991 Firica et al.
5,092,889 A 3/1992 Campbell, Jr.
5,312,426 A 5/1994 Segawa et al.
5,372,604 A 12/1994 Trott
5,374,268 A 12/1994 Sander
5,441,509 A 8/1995 Vidal et al.
5,487,746 A 1/1996 Yu et al.
5,507,747 A 4/1996 Yuan et al.
5,586,985 A 12/1996 Putnam et al.
5,709,682 A 1/1998 Medoff
5,718,704 A 2/1998 Medoff
5,931,839 A 8/1999 Medoff
5,935,128 A 8/1999 Carter et al.
5,941,878 A 8/1999 Medoff
6,066,141 A 5/2000 Dall et al.

(Continued)

*Primary Examiner* — Sameh Boles
(74) *Attorney, Agent, or Firm* — Tarolli, Sundheim, Covell & Tummino LLP

(57) ABSTRACT

The disclosure includes a bone plate extender and extension system. The system includes a first bone plate extender and may additionally include a bone fixation element and/or an additional bone plate. The bone plate extender may be affixed to a bone portion at one end, for instance, a fractured bone portion, via a bone fixation element, and associated with a second bone plate at an opposite end, so as to facilitate alignment and stabilization of the bone and thereby correct and treat a bone fracture. The bone plate extender may include an extended body, which includes a bone plate engagement portion, a bone fixation portion, and an intercalating portion there between. In certain variations, the extended body is planar, and in certain variations the extended body is angled, curved or arced. Methods of using such bone plate extension systems for the reduction, restoration and treatment of bone fractures are also provided.

16 Claims, 17 Drawing Sheets

(56) References Cited

U.S. PATENT DOCUMENTS 6,077,266 A 6/2000 Medoff
6,113,603 A 9/2000 Medoff
6,248,109 B1 6/2001 Stoffella
6,302,884 B1 10/2001 Wellisz et al.
6,302,887 B1 10/2001 Spranza et al.
6,440,135 B2 8/2002 Orbay et al.
6,464,710 B1 10/2002 Foster
6,554,835 B1 4/2003 Lee
6,652,530 B2 11/2003 Ip et al.
7,037,308 B2 5/2006 Medoff
7,090,676 B2 8/2006 Huebner et al.
7,189,237 B2 3/2007 Huebner
7,229,445 B2 6/2007 Hayeck et al.
7,235,079 B2 6/2007 Jensen et al.
7,250,053 B2 7/2007 Orbay
7,316,687 B2 1/2008 Aikins et al.
7,326,212 B2 2/2008 Huebner
2002/0095157 A1 7/2002 Bowman
2002/0143339 A1 10/2002 Medoff
2002/0147452 A1 10/2002 Medoff et al.
2004/0102776 A1* 5/2004 Huebner ........................ 606/69
2004/0158251 A1 8/2004 Morrison et al.
2004/0230312 A1 11/2004 Hanson et al.
2005/0070902 A1 3/2005 Medoff
2005/0154392 A1 7/2005 Medoff et al.
2005/0234458 A1 10/2005 Huebner
2005/0240187 A1* 10/2005 Huebner et al. ................ 606/69
2005/0245931 A1 11/2005 Orbay
2006/0015101 A1 1/2006 Warburton et al.
2006/0089648 A1 4/2006 Masini
2006/0155284 A1 7/2006 Doherty et al.
2006/0173458 A1 8/2006 Forstein et al.
2006/0189992 A1 8/2006 Medoff
2006/0241612 A1 10/2006 Medoff
2007/0118126 A1 5/2007 Medoff et al.
2007/0123880 A1 5/2007 Medoff
2007/0173841 A1 7/2007 Ralph et al.
2009/0043310 A1 2/2009 Rasmussen

* cited by examiner

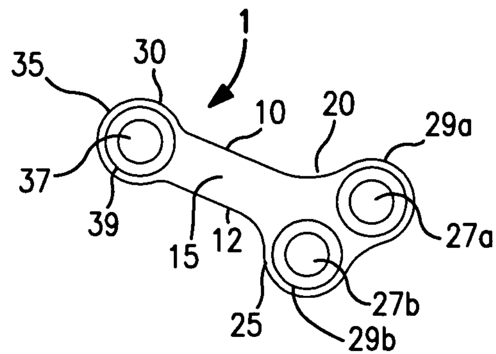
FIG. 1C
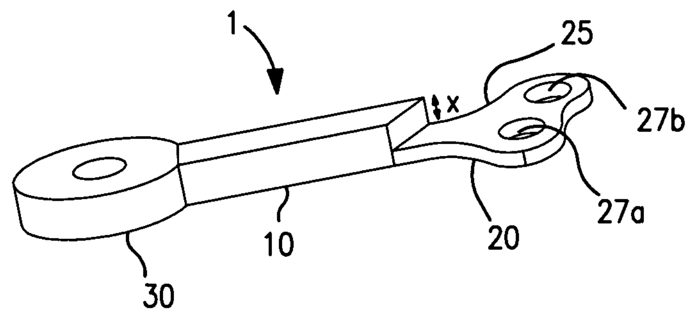
FIG. 1D
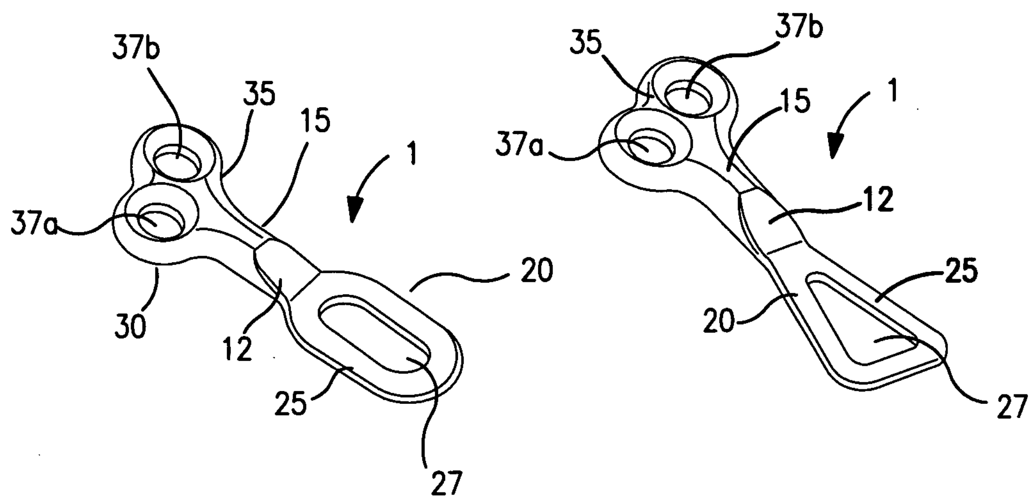
FIG. 1E
FIG. 1F

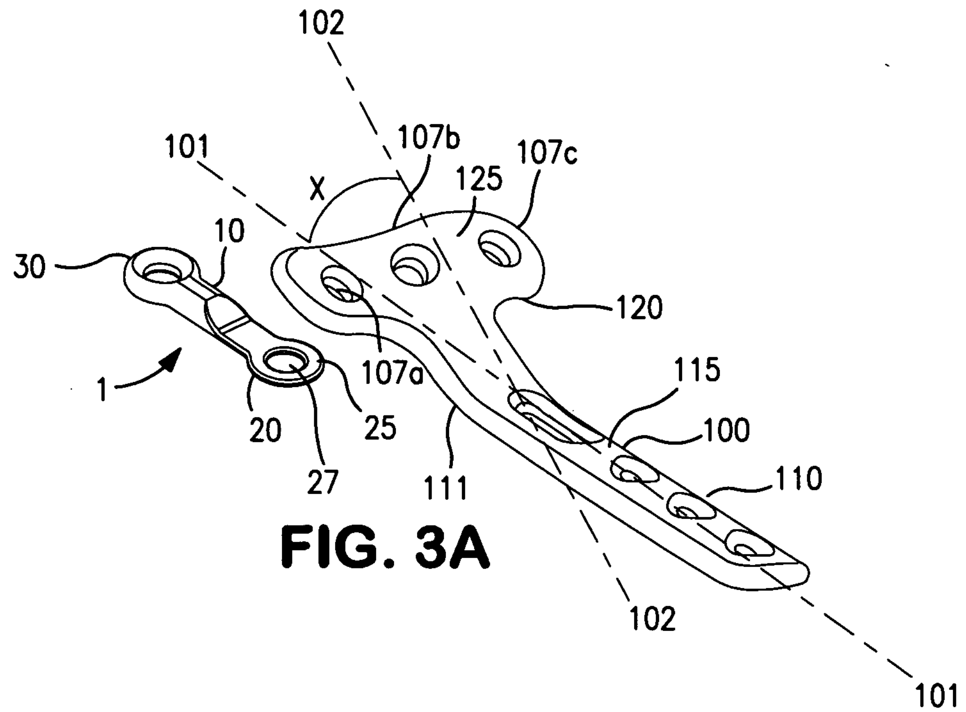
FIG. 3A
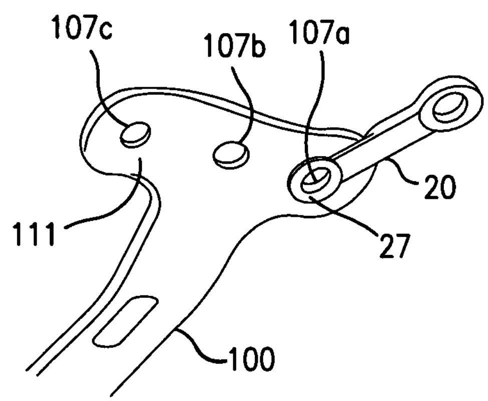
FIG. 3B
20
100
FIG. 3C

BONE PLATE EXTENDER AND EXTENSION SYSTEM FOR BONE RESTORATION AND METHODS OF USE THEREOF

BACKGROUND

A bone fracture is a condition of a bone in which at least a portion of the bone has cracked, broken, and or fragmented. Bone fractures can be caused in several different ways, for instance, as a result of a high force impact, stress, or as the result of conditions that presuppose the bones for fracturing, such as osteoporosis, cancer, and the like. Fractures may be closed or compound and they may be simple or multi-fragmentary, e.g., comminuted.

The ease and success of treatment of bone fractures often depends on the type and location of the fracture and the tools available for correcting the crack, break, and/or fragmentation of the bone to be treated. For instance, a closed, simple fracture along a diaphyseal portion of a long bone may be relatively simple to correct and therefore treat. However, a distal fracture of the distal radius, e.g., a Colles' fracture, due to its location and the morphology of the bones involved, may be difficult to correct and treat.

There are several methods for treating bone fractures, all of which typically involve the stabilization of the bone fragments. For instance, the fractured bone pieces may be reduced, e.g., aligned, and restored to their natural position, which position is then maintained using standard immobilization techniques, such as using plaster or fiberglass casts, as well as implanting surgical nails, screws, plates, and wires which function to fix and hold the fractured bone together.

However, the use of casts and typical surgical nails, screws, plates, and wires for the treatment of fractured bones have several drawbacks. For example, casts are problematic in that they are big, bulky and usually only allow a small degree of motion of associated joints. Further, casts often fail to provide adequate internal fixation, thus, resulting in pain, deformity, and/or prolonged disability. Additionally, the use of typical nails, screws, plates, and wires can be problematic because these devices may be hard to apply, are not easily manipulated so as to appropriately reduce and fix the bone in correct alignment, and are not suited for reducing fragments that are displaced from the main loci of the fracture.

The details of one or more variations of the subject matter described herein are set forth in the description below and the accompanying drawings. Other features and advantages of the subject matter described herein will be apparent from the description and drawings, and from the claims.

SUMMARY

Aspects of the present disclosure include a bone plate extender and a bone plate extension system. The bone plate extension system may include at least a first bone plate extender and may additionally include a bone fixation element and/or an additional bone plate. Accordingly, in one aspect, the present disclosure is directed to a bone plate extender, which bone plate extender may be affixed to a bone portion at one end, for instance, a fractured bone portion, e.g., via a bone fixation element, and associated with a second bone plate, e.g., another bone plate extender and/or a primary bone plate, at an opposite end, so as to facilitate alignment and stabilization of the bone and thereby correct and/or treat a bone fracture.

For instance, in certain variations, the bone plate extender includes an extended body. The extended body includes a bone plate engagement portion, a bone fixation portion, and an intercalating portion there between. In certain variations, the extended body or a portion thereof may be planar, and in certain variations the extended body may be angled, curved, or arced.

The bone plate engagement portion includes a bottom surface and a top surface. In some embodiments, the top or bottom surface may be planar or non-planar, and either surface may be configured for contacting a bottom or a top surface of an additional bone plate, e.g. a primary bone plate. In certain variations, the bone plate engagement portion includes an opening extending between the bottom and top surfaces, such as an opening that may be configured for receiving a fastener there through. In certain variations, the bone plate engagement portion may be angled with respect to one or more of the intercalating and/or bone fixation portions.

The bone fixation portion includes a bottom surface and a top surface, wherein the top surface may be planar or non-planar and the bottom surface may be configured for contacting a bone portion, e.g., a displaced distal radial styloid bone portion. In certain variations, the bone plate engagement portion includes an opening extending between the top and bottom surfaces, such as an opening that may be configured for receiving a fastener there through. In certain variations, the bone fixation portion may be angled with respect to one or more of the intercalating and/or bone plate engagement portions.

The intercalating portion includes a top surface and a bone contacting surface. Further, the intercalating portion includes a proximal portion including a proximal end, a distal portion including a distal end, and an intermediary portion positioned between said proximal and said distal portions. In certain variations, the intercalating portion may be planar, and in certain variations, the intercalating portion may be non-planar.

In certain variations, the top surface corresponds to a primary plane, and in certain variations, the bone contacting surface corresponds to a primary plane. In certain variations, the top surface or bone contacting surface includes a plurality of planes, e.g., secondary planes, tertiary planes, etc., for instance, where the top or bone contacting surface includes an internal angle, curve, or arc. For example, in certain variations, the proximal portion of the intercalating portion corresponds to a primary plane, the distal portion corresponds to a secondary plane, and the primary and secondary planes are out of plane with one another, such as where the proximal portion may be angled with respect to the distal portion.

In certain variations, the distance between the top and bottom surface of the proximal portion, for instance, the bone plate engagement portion, corresponds to a first thickness. In certain variations, the distance between the top and bone contacting surface of the intercalating portion corresponds to a second thickness. In certain variations, the distance between the top and bottom surface of the distal portion, e.g., the bone fixation portion, corresponds to a third thickness. In certain variations, the first, second, and third thickness are all the same, and in certain variations, they are all different. In certain variations, at least one of the first, second, and third thickness may be different from one or more of the other thicknesses, for instance, in one variation, the second thickness may be greater than the first and/or third thickness. In certain variations, the intercalating portion corresponds to the transition zone between the proximal and distal portions and includes a thickness that gradually increases/decreases from the proximal to the distal portions.

Further, in one aspect, the present disclosure is directed to a bone fixation element, such as a fastener, which bone fixation element includes an extended body. In certain variations, the extended body includes a proximal portion including a proximal end, a distal portion including a distal end, and an elongate portion extending between said proximal and distal portions. In certain variations, the proximal portion includes a shaft, wherein the shaft includes at least one smooth region and at least one threaded region. In certain variations, the smooth region may be positioned between the proximal end and the threaded region and may include a length that corresponds to a thickness of a bone plate, e.g., a primary or extender bone plate. In certain variations, the threaded region includes locking screw threads and may include a length that corresponds to a thickness of a bone plate, e.g., a primary or extender bone plate. In certain variations, the proximal end being configured for engaging a top surface of a bone plate. The elongate portion may or may not include threading and the distal portion may be conical in shape and tapered such that the distal end forms a point.

Furthermore, in one aspect, the present disclosure is directed to a method of using a bone plate extender in conjunction with a bone plate, e.g., another bone plate extender and/or a primary bone plate, so as to reduce a bone fracture. In certain variations, the method includes, in any logical order, attaching a first bone plate to a first bone portion, attaching a bone plate extender of the subject disclosure to a second bone portion, and attaching the bone plate extender to the first bone plate in a manner sufficient to reduce the bone fracture. It is to be noted that the bone plate extender may be used as a sole bone fixation device or in conjunction with a second bone plate. Additionally, the bone plate extender may span two portions of the same fractured bone or portions of two different bones.

BRIEF DESCRIPTION OF THE DRAWINGS

According to common practice, the various features of the drawings may not be presented to-scale. Rather, the dimensions of the various features may be arbitrarily expanded or reduced for clarity. Included in the drawings are the following figures:

FIG. 1 depicts a planar or non-angled bone plate extender of the subject disclosure that includes an extended body, which extended body includes a bone plate engagement portion, a bone fixation portion, and an intercalating portion there between, wherein neither of the bone plate engagement portion or the bone fixation portion are angled with respect to the intercalating portion or each other. FIG. 1C depicts a bone plate extender, wherein the bone fixation portion includes two recessed openings. FIG. 1D depicts a bone plate extender, wherein the bone plate engagement portion includes a plurality of openings, e.g., two. FIGS. 1E and 1F depict a bone plate extender, wherein the bone plate engagement portion includes an extended, non-circular opening.

FIG. 2 depicts a bone plate extender of the subject disclosure that includes an extended body, which extended body includes a bone plate engagement portion, a bone fixation portion, and an intercalating portion there between, wherein at least one of the bone plate engagement portion, the intercalary portion, and/or the bone fixation portion is angled with respect to one another so as to allow placement of the bone plate in such a manner that the proximal and distal portions may be in or out of plane from one another.

FIG. 3 depicts how the bone plate extender of FIG. 1B may be associated with another bone plate. FIG. 3A depicts a bone plate extender and a bone plate before the two bone plates are aligned for coupling. FIG. 3B depicts a bone plate extender appropriately aligned for coupling with a proximal portion of a primary bone plate. FIG. 3C depicts a side view of the bone plate extender and bone plate of FIG. 3B.

FIG. 4 depicts how the bone plate extender of FIG. 1C may be associated with another bone plate, e.g., a primary bone plate.

FIG. 5 depicts how the bone plate extender 1 of FIG. 1I may be associated with another bone plate, e.g., a primary bone plate.

FIG. 6 depicts a primary bone plate having one or a plurality of bone plate extenders associated therewith.

FIG. 8 depicts a bone plate system that includes a primary bone plate and a bone plate extender which system may be applied to one or more bone portions such as a fractured and displaced radial styloid portion.

FIG. 10 depicts a bone plate system. FIG. 11 illustrates another embodiment of a bone plate extender in conjunction with a bone plate system of the disclosure. Specifically, a top perspective view of a primary bone plate and a bone plate extender is provided. The primary bone plate has the configuration of a "T," and the bone plate extender has a bent and twisted configuration.

FIG. 12 illustrates another embodiment of a bone plate system of the disclosure.

Like reference symbols in the various drawings indicate like elements.

DEFINITIONS

Figure 1A:
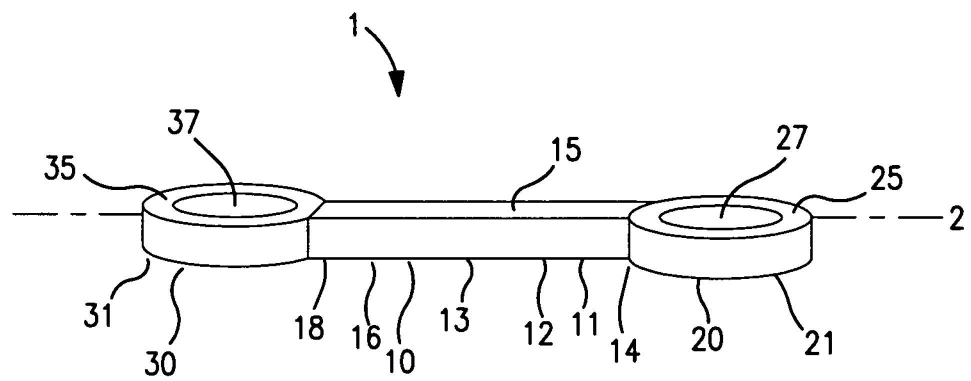
FIG. 1A depicts a bone plate extender wherein the bone plate extender includes a single thickness.

Before the present subject matter is further described, it is to be understood that this subject matter described herein is not limited to particular embodiments described, as such may of course vary. It is also to be understood that the terminology used here in is for the purpose of describing particular embodiments only, and is not intended to be limiting. Unless defined otherwise, all technical terms used herein have the same meaning as commonly understood by one skilled in the art to which this subject matter belongs.

Where a range of values is provided, it is understood that each intervening value, to the tenth of the unit of the lower limit, unless the context clearly dictates otherwise, between the upper and lower limit of that range, and any other stated or intervening value in that stated range, is encompassed within the subject matter described herein. The upper and lower limits of these smaller ranges may independently be included in the smaller ranges, and are also encompassed within the subject matter described herein, subject to any specifically excluded limit in the stated range. Where the stated range includes one or both of the limits, ranges excluding either or both of those included limits are also included in the subject matter described herein.

It must be noted that as used herein and in the appended claims, the singular forms "a", "and", and "the" include plural referents unless the context clearly dictates otherwise. Thus, for example, reference to a "fastener" includes a plurality of such fasteners, and reference to "the opening" includes reference to one or more openings and equivalents thereof known to those skilled in the art, and so forth.

It is further noted that the claims may be drafted to exclude any optional element. As such, this statement is intended to serve as antecedent basis for use of such exclusive terminology as "solely", "only" and the like, in connection with the recitation of claim elements, or the use of a "negative" limitation. Accordingly, the term "optional" or "optionally present"—as in an "optional element" or an "optionally present element" means that the subsequently described element may or may not be present, so that the description includes instances where the element is present and instances where it is not.

As will be apparent to those of skill in the art upon reading this disclosure, each of the individual embodiments described and illustrated herein has discrete components and features which may be readily separated from or combined with the features of any of the other several embodiments without departing from the scope of the subject matter described herein. Any recited method can be carried out in the order of events recited or in any other order which is logically possible.

DETAILED DESCRIPTION

Aspects of the present disclosure include a bone plate extension system. The bone plate extension system may include at least a first bone plate extender and may additionally include a bone fixation element and/or an additional bone plate. Accordingly, in one aspect, the present disclosure is directed to a bone plate extender, which bone plate extender may be affixed to a bone portion at one end, for instance, a fractured bone portion, e.g., via a bone fixation element, and associated with a second bone plate, e.g., a primary bone plate, and/or a second bone portion at an opposite end, so as to facilitate alignment and stabilization of the bone and thereby correct and/or treat a bone fracture. For instance, in certain variations, the bone plate extender includes an extended body. The extended body includes a proximal portion that may include a bone plate engagement portion, a distal portion that may include a bone fixation portion, and an intercalating portion there between. In certain variations, the extended body may be planar, and in certain variations the extended body may be angled, curved or arced.

Further, in another aspect, the present disclosure is directed to a bone fixation element, e.g., a fastener, which bone fixation element includes an extended body. In certain variations, the extended body includes a proximal portion including a proximal end, a distal portion including a distal end, and an elongate portion extending between said proximal and distal portions. In certain variations, the proximal portion includes a shaft, wherein the shaft includes at least one smooth region and at least one threaded region, wherein the smooth region may be positioned between the proximal end and the threaded region and may include a length that corresponds to a thickness of a bone plate, e.g., a primary or extender bone plate.

Furthermore, in an additional aspect, the present disclosure is directed to a method of using a bone plate extender in conjunction with a bone plate, e.g., a primary bone plate, so as to reduce a bone fracture. In certain variations, the method includes, in any logical order, attaching a primary bone plate to a first bone portion, attaching a bone plate extender of the subject disclosure to a second bone portion, and attaching the bone plate extender to the primary bone plate in a manner sufficient to reduce the bone fracture.

The various aspects of the subject bone plate extension system, including the plate extender and bone fixation element, will be described first, followed by a description of the uses thereof, e.g., for the reduction and/or fixation of bone portions for the restoration and/or treatment of bone fractures.

Bone Plate Extender and Extension System

As summarized above, the present disclosure provides for a bone plate extender and/or a bone plate extension system. In certain aspects, the bone plate extension system may include one or more bone plate extenders, a bone fixation element, and in certain instances, a second bone plate, one or more of which may be employed to reduce and/or fix one or more bone portions for the treatment of a bone fracture, for example.

Accordingly, in one variation, the bone plate extension system includes at least a bone plate extender, a second bone plate, and a bone fixation element. The bone plate extender may be configured for being attached to one or more bone portions, e.g., via a bone fixation element, as disclosed herein, and may be adapted to be coupled with another bone plate, e.g., another bone plate extender or a primary bone plate, so as to reduce, fix and/or stabilize one or more bone portions in healing alignment for the treatment of a bone fracture.

In certain variations, the bone plate extender may be planar and in certain variations the bone plate extender may be configured such that at least one surface thereof may be at an angle with respect to a second bone plate to which the extender plate is to be coupled. For instance, one or more surfaces of the bone plate extender may include a curvature or angle such that a plane of the surface may be angled with respect to a plane of a surface of the second bone plate. Accordingly, the bone plate extender, may have a variety of configurations ranging from planar to non-planar in relationship to a second bone plate to which the extender plate is to be coupled. At least in this manner, the bone plate extender and/or extension system may be readily adaptable to bone portions of varying morphologies.

For example, due to the adaptability of the bone plate extender to differing bone morphologies, the bone plate extender is well suited for being associated with a displaced bone fracture, such as a fractured distal radial styloid portion that is displaced in a volar or dorsal direction, and additionally coupled to a secondary bone plate, such as another bone plate extender and/or a primary bone plate, for instance, a primary bone plate positioned along a diaphyseal portion of a radius bone. The bone plate extender and secondary bone plate may be attached to respective bone portions and be coupled together for the purpose of reducing and fixing comminuted fractures, wherein the fracture includes a fragmented bone portion that may be distal to a primary bone shaft portion and/or positioned at an angle thereto. For example, the present bone plate extension system may be configured so as to reduce and align fragmented bone portions wherein the fragmented bone portions are comminuted and/or distanced and out of plane from one another.

A bone plate extender or other bone plate of the subject bone plate system may be fabricated from any suitable biocompatible material so long as the bone plate(s) is of sturdy yet malleable construction. For instance, in certain embodiments, a bone plate extender or other bone plate may be fabricated from a suitable metal material containing a metal such as stainless steel, titanium, cobalt chromium, and/or an alloy thereof. Further, suitable materials may be a bioabsorbable material such as polygalactic acid (PGA), polylactic acid (PLA), copolymers thereof, and the like. Other suitable materials include plastic, ceramics, and the like. In general, the bone plate extender may be fabricated from a suitable material so as to be stiffer and stronger than the section of bone spanned by the extender plate, yet flexible enough not to significantly strain the bone. In certain embodiments, a bone plate extender may be fabricated in accordance with methods including stamping, machining, casting, laser cutting, molding, and the like.

In certain variations, the bone plate extension system may be configured such that a bone plate extender may be attached, e.g., at a distal or bone fixation portion, to a fractured bone portion, for instance, in a periarticular, juxta-articular and/or metaphyseal bone region, which bone portion may be located distally from a diaphyseal bone portion. For instance, the distal or bone fixation portion of the bone plate extender may be configured so as to closely model the contour of a periarticular, juxta-articular, and/or metaphyseal bone region and may additionally include an opening that may be adapted for receiving a fastener, such as a bone fixation element disclosed herein, which fastener may be inserted through the opening and into the fractured bone portion, e.g., in the periarticular, juxta-articular and/or metaphyseal bone region, thereby attaching the bone plate extender to the fractured bone portion.

Additionally, the bone plate extender may be configured for being associated with a second bone plate, for instance, another bone plate extender and/or a primary bone plate, such as a primary bone plate that may be positioned along a diaphyseal portion of a long bone. For instance, the bone plate extender may include a proximal or bone plate engagement portion, which portion includes an opening that may be aligned with a corresponding opening in another bone plate extender or primary bone plate and be adapted to receive a fastener. The bone plate engagement portion may be configured for being associated with a top or a bottom surface of another bone plate. In certain variations, the bone plate engagement portion may be configured for being slid or otherwise positioned underneath the second bone plate, and in certain variations the bone plate engagement portion may be configured for being positioned on top of the second bone plate, and may further be adapted for coupling and/or attachment therewith. For example, a bone fixation element disclosed herein, which fastener may be inserted through the opening in the second bone plate and into the bone plate extender, thereby associating the bone plate extender with the primary bone plate, and in some instances, a bone portion, thus, not only securing the bone plate extender to the second bone plate, but also securing both bone plates to the bone.

In this manner, the bone plate extender may be configured for being attached to a fractured bone portion and associated with a second bone plate, such as any of a wide variety of bone plates currently available on the market, so as to properly align and reduce the bone fracture via attachment to the primary one plate. Specifically, the configuration of the bone plate extender may be such that it may be configured for both being attached to a distally located fracture portion and may also be adapted so as to be associated with a wide range of bone plates that are presently commercially available, such that the two plates may be coupled so as to correctly reduce, align, stabilize, and/or restore a fractured bone portion to a position that at least approximates its natural position and thereby treats the bone fracture. Accordingly, given the adaptable configurations of the various portions of the bone plate extender, the present system is capable of reducing and fixing a bone fracture, such as a fracture of the radius bone, wherein a portion of the fragmented bone resides in a position that may be distal to a primary bone portion, such as where the fragment resides within the distal styloid process platform of the radius bones.

Hence, a subject bone plate extender and/or system of the present disclosure may have a variety of configurations adapted to capture fracture fragments, which are distanced from one another and reduce the fragmented portion(s) in correct alignment with a primary non-fractured bone portion so as to stabilize the fracture portions and facilitate the appropriate healing of the fractured and/or fragmented bone. In this manner, the bone plate system provides a flexible interface for reducing and stabilizing fractures, including periarticular fractures that are out of plane from a main, primary bone shaft.

For instance, the subject bone plate extender and/or system may be adapted to be attached to a wide range of bone positions, including along a radial bone shaft and/or along a radial platform, and/or along an internal or external surface of the radial bone shaft, so as to stabilize and reduce a bone fracture there between. For example, where a fracture includes a volar or dorsally displaced distal radius fracture, a first bone plate, which may be included in the system, e.g., a proximal or diaphyseal bone plate, may be positioned centrally along the diaphyseal portion of the radius. In such an embodiment, a bone plate extender of the system, which may include a configuration adapted to the juxtaarticular bone morphology of the radial styloid (e.g., the bone plate extender may include an internal angle or arc that recapitulates a desired angle of the volar radius), may be positioned along a fractured and/or displaced distal radius portion, e.g., a dorsally displaced distal radius fragment.

Accordingly, by first attaching the bone plate(s) of the system to respective bone portions and then coupling the plates together, a fracture of the distal radius styloid may be properly aligned and reduced so as to establish a natural reduction of the radius platform. Additionally, the number, position, and configuration of the openings of the bone plate extender may further add to the flexibility of the system by allowing relative movement of the bone plate extender and a second bone plate until a desired orientation has been achieved and the plates locked into position relative to each other.

In one aspect, the present disclosure is directed to a bone plate extender, which bone plate extender may be configured for being affixed to a bone portion at one end, for instance, a fractured bone portion, e.g., via a bone fixation element, and associated with a second bone plate, e.g., another bone plate extender and/or a primary bone plate, at an opposite end, so as to facilitate alignment and stabilization of the bone and thereby correct and/or treat a bone fracture. Accordingly, a bone plate extender of the subject disclosure may have any suitable shape and have any suitable size so long as the bone plate extender may be capable of being associated with a bone portion, e.g., a fractured bone portion, and of being coupled to a second bone plate so as to assist in the reduction and/or stabilization of one or more bone portions and thereby treat a bone fracture.

For instance, the bone plate extender may be an elongate plate member with an extended body that includes a proximal portion with a proximal end, a distal portion with a distal end, and an intercalating portion between the proximal and distal portions. Specifically, the first and second ends are separated from one another, which separation defines a length of the subject plate.

In certain variations, and dependent on the context, a proximal portion of the bone plate extender refers to a region of the bone plate extender that contains a portion that may be configured for being coupled to another bone plate and/or attached to a portion of bone, e.g., a first bone portion. Hence, the proximal portion of the bone plate extender may be referred to herein as a bone plate engagement portion, because this portion may be configured for engaging, e.g., being coupled with, a second bone plate.

In certain variations, and dependent on the context, a distal portion of the bone plate extender refers to a region of the bone plate extender that contains a portion that may be configured for being associated with another portion of bone, for instance, a distally displaced fractured bone portion. Hence, the distal portion of the bone plate extender may be referred to herein as a bone fixation portion, because this portion may be configured for being contacted and/or associated with, e.g., attached to, another bone portion, e.g., a second bone portion. It is to be noted that the first and second bone portion may be different portions of the same bone, or may be portions of separate bones.

Additionally, the bone plate extender includes a top and a bottom surface, wherein the top and bottom surface are separated from one another, the separation of which defines a thickness. In certain embodiments, the bone plate extender includes a bottom surface that may be configured for contacting a bone surface and therefore may be referenced as a bone contacting surface. Likewise, in certain embodiments, the bone plate extender includes a top surface that is opposite the bone contacting surface.

Accordingly, the bone plate engagement portion of the bone plate extender includes a bottom surface and a top surface. In certain variations, the top surface of the bone plate engagement portion may be configured for contacting a bone contacting surface of an additional bone plate, e.g., a primary bone plate, and In certain variations, the bottom surface of the bone plate engagement portion may be configured for contacting a top surface of a primary bone plate. Accordingly, the bone plate extender may be configured for being associated with a top or a bottom surface of a second bone plate. In certain variations, the top and/or bottom surface of the bone plate engagement portion may be substantially planar or non-planar.

The bone fixation portion also includes a bottom surface and a top surface. The top or bottom surface may be planar or non-planar and may be configured for contacting a bone portion, e.g. a displaced distal radial styloid portion. In certain variations, the bone plate engagement portion includes a morphology that may be adapted to closely fit the morphology of a bone fracture portion located in a juxtaarticular or metaphyseal bone region.

The intercalating portion of the bone plate extender also includes a top surface and a bone contacting surface. Further, the intercalating portion may include a proximal portion including a proximal end, a distal portion including a distal end, and an intermediary portion positioned between said proximal and said distal portions. In certain variations, the length of the intercalating portion may be fixed. In certain variations, the length of the intercalating portion may be adjustable.

For example, the bone plate extender, e.g., an intercalating portion thereof, may include a slot and/or grove configuration, whereby the proximal and distal portions of the bone plate could be moved relative to one another. For instance, the proximal and distal portions forming the slot could have a male to female relationship relative to one another, and the slot could be configured to accommodate a screw, such that a desired length of the bone plate extender could be adjusted by sliding the proximal and distal portions relative to one another and locking the desired length by inserting a screw within the slot, which screw functions to prevent any further movement of the proximal and distal portions relative to one another. In this manner the length of the intercalating portion, and the plate extender as a whole, could be adjustable.

In certain embodiments, the bone plate extender, e.g., an intercalating portion thereof, may be malleable or flexible, and thus may be capable of being bent or formed intraoperatively to accommodate the shape of the bone. However, in certain embodiments, the intercalating portion is configured so as to resist deformation. For instance, the strength of the material used to form the bone plate extender, e.g., an intercalating portion thereof, may be selected such that the material and the portion from which it is made is such that it resists deformation. Further, the shape of the bone plate extender may be such that it provides additional strength so as to resists deformation.

In certain variations, the intercalating portion may be planar, and in certain variations, the intercalating portion may be non-planar. For instance, in certain variations, the top surface of the intercalating portion corresponds to a primary plane, and in certain variations, the bone contacting surface of the intercalating portion corresponds to a primary plane. In certain variations, the top surface or bone contacting surface includes a plurality of planes, e.g., secondary, tertiary, etc., for instance, where the top or bone contacting surface includes an internal angle, curve, or arc. For example, in certain variations, the proximal portion of the intercalating portion corresponds to a primary plane, the distal portion corresponds to a secondary plane, and the primary and secondary planes are out of plane with one another, such as where the proximal portion may be angled with respect to the distal portion. In this manner, the configuration of the intercalary portion may vary so as to allow the bone plate extension to be place in or out of plane with respect to a bone fracture and/or a second bone plate. In certain variations, the bone plate engagement portion may be angled with respect to the intercalating portion. In certain variations, the bone fixation portion may be angled with respect to the intercalating portion.

In certain variations, the distance between the top and bottom surface of the bone plate engagement portion corresponds to a first thickness. In certain variations, the distance between the top and bone contacting surface of the intercalating portion corresponds to a second thickness. In certain variations, the distance between the top and bottom surface of the bone fixation portion corresponds to a third thickness. In certain variations, the first, second, and third thickness are all the same, and in certain variations, they are all different. In certain variations, at least one of the first, second, and third thickness may be different from one or more of the other thicknesses. For instance, the first thickness may be greater or less than the second and/or third thickness, or the second thickness may be greater or less than the first and/or third thickness, or the third thickness may be greater or less than the first and/or second thickness. In certain embodiments, the thickness of the intercalating portion varies so as to gradually increase/decrease from a proximal to distal portion of the elongated body thereof.

For instance, in certain variations, the various portions of the bone plate extender may have a thickness that may range from about 0.01 mm to about 5 mm, for instance, between about 0.01 mm or less to about 3 mm or more, such as between about 0.5 mm or about 1 mm to about 2 or about 2.5 mm, wherein the thickness of each portion may be substantially the same, or one or more of the thicknesses may differ from the others. In certain variations, the bone plate extender may have a length that ranges from about 5 mm or less to about 60 mm or more, such as about 7 mm to about 50 mm, for instance, between about 9 mm or 10 mm to about 25 mm, such as between about 12 mm to about 15 mm or 20 mm. In certain variations, the bone plate extender includes at least a first side and a second side which sides are separated from each other by a distance, which distance defines a width. A suitable width may range from about 1 mm or less to about 50 mm or more, for instance, between about 3 mm to about 25 mm, such as between about 5 mm or about 7 mm to about 15 mm or about 20 mm, for instance, about 8 mm to about 10 mm.

Accordingly, in certain variations, the bone plate extender may be configured for being associated with, e.g., contacted with and/or attached to, another bone plate, such as a primary bone plate, and/or a bone portion, e.g., a diaphyseal bone portion, and so the bone plate extender includes a bone plate engagement portion. The bone plate engagement portion of the bone plate extender may have any suitable configuration so long as the bone plate engagement portion is capable of facilitating the association of the bone plate engagement portion with the other bone plate. Hence, in certain variations, the bone plate engagement portion of the bone plate extender includes at least one opening extending between the bottom and top surfaces, such as an opening that may be configured for receiving a fastener there through, such as a fastener that may be inserted through the opening and which functions to couple the bone plate extender to one or more of an additional, e.g., primary, bone plate and/or a bone portion.

The at least one opening of the bone plate engagement portion of the bone plate extender may be of any suitable configuration so long as it facilitates the coupling of the bone plate extender to an additional bone plate. The opening may be round, circular, semi-circular, arced, oval, elliptical, elongated, triangular, square, rectangular, and the like. For instance, in certain variations, the at least one opening includes a plurality of openings, such as 2, 3, 4, or 5 openings. Where a plurality of openings are included, the openings may be in line with one another, or offset from one another.

In certain variations, the bone plate engagement portion includes a flattened, planar portion that includes an opening, such as a circular, ovoid, or triangular opening, wherein the thickness of the flattened, planar portion may be substantially less than the thickness of an intercalating or bone fixation portion of the bone plate extender. At least in this manner, the bone plate engagement portion may be configured for being fit beneath or on top of a bottom or top surface, respectively, of a second bone plate. Further, in such an instance, the thickness of the intercalating or bone fixation portion(s) may correspond to the thickness of the second bone plate, such that when the bone plate engagement portion may be associated with the second bone plate, e.g., contacted with a bone contacting surface of the second bone plate, the height of the intercalating and/or bone fixation portions of the bone plate extender substantially corresponds to the height of the second bone plate so that the top surface of the intercalating and/or bone fixation portions may be flush with the top surface of the second bone plate.

In certain variations, the bone plate extender may be configured for being associated with, e.g., contacted with and/or attached to, a bone portion, such as a juxtaarticular or metaphyseal bone portion, and so the bone plate extender includes a bone fixation portion. The bone fixation portion of the bone plate extender may have any suitable configuration so long as the bone fixation portion may be capable of facilitating the association of the bone fixation portion with a bone portion. Hence, the bone fixation portion may include a configuration adapted to a particular bone morphology and/or may include at least one opening extending between the bottom and top surfaces thereof, such as an opening, which opening may be configured for facilitating the attachment of the distal portion of the bone plate extender to a bone portion, e.g., via a fastener inserted there through.

The at least one opening of the bone fixation portion of the bone plate extender may be of any suitable configuration so long as it facilitates the coupling of the bone plate extender to a bone portion. The opening may be round, circular, semi-circular, arced, oval, elliptical, elongated, triangular, square, rectangular, and the like. For instance, in certain variations, the at least one opening includes a plurality of openings, such as 2, 3, 4, or 5 openings. Where a plurality of openings are included, the openings may be in line with one another, or offset from one another. For example, in certain variations, two openings may be included wherein the center of one opening may be further from a proximal end of the bone plate than the center of the second circle. In certain variations, three or four openings are included wherein the openings are in the formation of a clover leaf.

The one or more openings referenced herein may span the entire thickness of the bone plate extender and extend between a bone contacting surface and a top surface thereof. The opening may be recessed and include threading such as threading that corresponds to the threading positioned on a fastener. In this manner, a fastener may be inserted into and through the opening by rotating the fastener in such a manner that the threads of the fastener align with the corresponding threads of the opening. In certain variations, the one or more openings do not include threading such that the fastener may be inserted there through without threading the fastener into the opening. The openings may be configured for receiving a fastener, such as a fixed or variable angle locking or non-locking fastener, and/or a fixed angle terminal device such as a blade plate.

As described above, in some instances, the bone plate extender may be configured for being associated with, e.g., contacted with and/or attached to a bone portion, for instance, a periarticular, metaphyseal and/or epiphyseal bone portion. For example, in certain variations, the bone plate extender may include a bone fixation portion that may be configured for being attached to an articulated bone morphology of a metaphysis or epiphysis bone portion, e.g., a juxta-articular portion, hence, the bone fixation portion may be configured so as to be complimentary to a such articulated bone portion. Thus, in certain variations, the bone fixation portion has a configuration that may be complimentary to a non-planar portion of an articulated bone portion.

For instance, in certain variations, the bone fixation portion may have a configuration that may be adapted to conform to a specific bone morphology, such as a configuration that is adapted to specifically and snugly fit the bone morphology to which the bone plate extender is to be contacted, associated, and/or attached. Thus, in certain variations, the bone plate extender may be non-planar. Consequently, in certain variations, there may be an angle at least between one or more of the proximal and distal portions of the bone plate extender.

For example, in certain embodiments, a top or bone contacting surface of a proximal portion of a bone plate extender, e.g., a bone plate engagement portion, may constitute a first or proximal plane of the bone plate extender, and a top or bone contacting surface of a distal portion of a bone plate extender, e.g., a bone fixation portion, may constitute a second or distal plane of the bone plate extender, wherein the proximal and distal planes of the bone plate extender are transverse to one another. Further, in certain variations, a top or bone contacting surface of a intercalating portion of a bone plate extender, may constitute a first plane of the bone plate extender, and a top or bone contacting surface of a proximal and/or distal portion of a bone plate extender may constitute a second and/or third plane of the bone plate extender, wherein one or more of the planes of the bone plate extender are transverse to one another. Additionally, a proximal portion of the intercalating portion of the bone plate extender may constitute a first or proximal plane of the bone plate extender and a distal portion of a bone plate extender may constitute a second or distal plane of the bone plate extender, wherein the proximal and distal planes of the intercalating portion of the bone plate extender are transverse to one another.

Hence, in certain variations, the top or bone contacting surface between the proximal and distal portions and/or ends thereof of the bone plate extender may include an internal angled portion. Accordingly, in certain embodiments, the angle between the planes may range from about 1° to about 90°, such as from about 5° to about 45°, for instance from about 7.5° to about 30°, including from about 10° to about 20°, such about as 15°. Additionally, although there may be an angle between the proximal and distal portions of the bone plate extender or an intercalating portion thereof, in certain embodiments, the proximal portion of the bone plate extender is not angled with respect to a primary plane as defined by the primary bone plate. For instance, in certain embodiments, the proximal portion of the bone plate extender, e.g., a bone plate engagement portion, may be substantially coplanar with a primary plane of the second bone plate to which the bone plate extender is to be coupled.

Thus, in certain embodiments, the bone plate extender includes an internal angled, curved, and/or arced portion between the proximal and distal ends thereof and is therefore angled, curved and/or arced in correspondence to a bone surface to which the plate is to be associated so as to model the morphology of the bone surface. Hence, in certain embodiments, the top or bone contacting surface between the proximal and distal ends of the bone plate extender may include an internal curved portion, wherein the curve includes a degree of curvature that ranges from about 10 mm to about 50 mm, for instance, between about 15 mm to about 35 mm, such as between about 18 mm or about 20 mm to about 25 or about 30 mm.

Further still, in certain embodiments, the top or bone contacting surface between the proximal and distal ends of the bone plate extender may include an internal arced portion, wherein the arc includes a radius of curvature that may be constant, increasing, or decreasing, depending in part on the length of the intercalating portion of the bone plate extender. Accordingly, in certain embodiments, a top or bone contacting surface of the bone plate extender includes an arc that has a decreasing radius of curvature that ranges from about 10 mm to about 50 mm, for instance, between about 15 mm to about 35 mm, such as between about 18 mm or about 20 mm to about 25 or about 30 mm. In certain embodiments, the bone plate extender includes a curved and/or twisted portion whereby the twisted portion allows the bone plate extender to extend outward and away from a second bone plate so as to contact a bone surface that may be positioned distally and out of plane with a bone contacting surface and/or a primary plane of the primary bone plate.

Accordingly, in certain variations, the bone plate extender includes a bone fixation portion, e.g., a distal portion, that may be angled, curved, or arced, as described above, relative to an intercalating and/or a bone plate engagement portion, e.g., a proximal portion, wherein the bone plate engagement portion of the bone plate extender may be relatively planar in relation to a primary plane defined by a top or bone contacting surface of the bone plate to which the bone plate extender may be attached. In certain variations, the bone plate extender includes a bone plate engagement portion that may be angled, curved, or arced, as described above, relative to an intercalating and/or a bone fixation portion. Accordingly, a portion or the entire bone plate extender may be angled or curved with relationship to the primary bone plate.

For instance, in certain variations, the bone fixation portion of the bone plate extender may be angled with respect to the rest of the plate portions. Additionally, in certain variations, the bone plate engagement portion of the bone plate extender may be angled with respect to the rest of the plate portions. In certain embodiments, the angle may range from about 0° to about 90°, such as from about 5° to about 45°, for instance from about 7.5° to about 30°, including from about 10° to about 20°, such about as 15°. However, in certain embodiments, neither the bone fixation portion nor the bone plate engagement portion of the bone plate extender may be angled but rather the bone plate extender may be planar.

In view of the above, the bone plate extender may be angled in relationship to a second bone plate to which the bone plate extender may be attached in numerous ways such that the bone plate extender includes a bone contacting surface that corresponds to one or more planes or an arc that are provided at an angle or substantially perpendicular to a primary plane defined by a primary bone plate. Accordingly, in certain embodiments, the bone plate extender may be angled with respect to a plane defined by a second, e.g., primary, bone plate, wherein the angle may range from about 1° to about 90°, such as from about 5° to about 45°, for instance from about 7.5° to about 30°, including from about 10° to about 20°, such about as 15°.

In certain embodiments, the bone plate extender includes a curved or concave portion between the first and second sides thereof and is therefore curved relative to a central, longitudinal axis defined by the proximal and distal ends of the bone plate extender. For instance, the bone plate extender may include an internal concave portion between the first and second sides of the bone plate.

As summarized above, in certain variations, the subject bone plate extension system of the present disclosure includes a second bone plate, which second bone plate may be another bone plate extender or a primary bone plate. The second bone plate of the subject bone plate system may have any suitable shape and may have any suitable size so long as the bone plate may be capable of being attached to a bone portion and coupled to a bone plate extender so as to assist in the reduction and/or stabilization of one or more bone portions and thereby treat a bone fracture.

Where the second bone plate is a bone plate extender it may have the dimensions as described above with reference to a first bone plate extender. Where the second bone plate is a primary bone plate, the primary bone plate may be an elongate plate member that includes a proximal portion with a proximal end, a distal portion with a distal end, and an intercalating portion between the proximal and distal portions. Specifically, the first and second ends are separated from one another, which separation defines a length of the subject plate. Additionally, the primary bone plate includes a top and a bottom surface, wherein the top and bottom surface are separated from one another, the separation of which defines a thickness. In certain embodiments, the primary bone plate includes a bottom surface that may be configured for contacting a bone surface and therefore may be referenced as a bone contacting surface. Likewise, in certain embodiments, the primary bone plate includes a top surface that is opposite the bone contacting surface. Further, the primary bone plate includes a first side and a second side which sides are separated from each other by a distance, which distance defines a width.

In certain embodiments, the primary bone plate may have a length that ranges from about 3 mm to about 50 mm or more, such as about 5 mm to about 40 mm, for instance, between about 10 mm to about 30 mm, such as between about 15 mm to about 20 mm or about 25 mm. In certain embodiments, the primary bone plate may have a thickness that may range from about 0.01 mm to about 3 mm, for instance, between about 0.1 mm to about 2 mm, such as between about 0.5 mm or about 0.75 mm to about 1 mm or about 1.5 mm. A suitable primary bone plate of the subject disclosure may have a width that ranges from about 3 mm to about 50 mm, for instance, between about 5 mm to about 40 mm, such as between about 8 or about 10 mm to about 20 mm or about 35 mm, for instance, about 25 mm to about 30 mm. The length of the intercalating portion, e.g., the portion between the proximal and distal portions, may be fixed. In certain embodiments, the length of the intercalating portion may be adjustable. For instance, the intercalating portion may be configured for sliding in the proximal-distal direction so as to decrease and/or increase in length, as described above.

In certain embodiments, the primary bone plate may be planar, wherein the proximal and distal ends define a primary plane. Hence, in certain embodiments, at least one of the primary bone plate bone contacting surface and the primary bone plate top surface substantially corresponds to a primary plane. In certain embodiments, the primary bone plate may be non-planar, wherein the proximal and distal ends are out of plane with one another.

For instance, in certain variations, the proximal portion of the primary bone plate may be angled with respect to the distal portion of the primary bone plate. For instance, a plane defined by a top or bottom surface of the proximal portion of a primary bone plate may be angled with respect to a plane defined by a top surface of the distal portion of the primary bone plate. The angle between the planes defined by the two surfaces may range from about 1° to about 90°, such as from about 5° to about 45°, for instance from about 7.5° to about 30°, including from about 10° to about 20°, such about as 15°.

For example, the primary bone plate may have a configuration that is adapted to conform to a specific bone morphology, such as a configuration that is adapted to specifically and snugly fit the bone morphology to which the bone plate is to be associated and/or attached. Hence, in certain variations, the primary bone plate includes an internal angled and/or arced portion between the proximal and distal ends thereof and is therefore angled and/or arced in correspondence to a bone surface to which the plate is to be associated. In certain variations, the bone contacting surface between the proximal and distal ends of the primary bone plate may include an internal arced portion, wherein the arc includes a radius of curvature that ranges from about 1 mm to about 50 mm, for instance, from about 5 mm to about 30 mm, including from about 10 mm to about 20 mm, such about as 15 mm.

Further, in certain instances, the primary bone plate includes a curved portion between the first and second sides thereof and is therefore curved relative to a central, longitudinal axis defined by the proximal and distal ends of the primary bone plate. For instance, the primary bone plate may include an internal concave portion between the first and second sides of the bone plate. The concaved portion may run along a partial or entire length of the primary bone plate, wherein the curvature comprises a degree of curvature, e.g., a concavity, that ranges from about ⅛ inch radius to about a 2 inch radius, from about ¼ inch radius to about 1½ inch radius, including about ½ inch radius to about a 1 inch radius. In certain variations, the primary bone plate may not be angled, arced, or curved, but rather may be planar.

The primary bone plate may be configured for being associated with, e.g., attached to, a shaft portion of a long bone. For instance, the primary bone plate may be configured for being attached to a diaphyseal portion of a bone, and therefore, the primary bone plate may be referenced as a diaphyseal bone plate. Hence, the primary bone plate, e.g., a diaphyseal plate, may be configured so as to be complimentary to a bone morphology, such as the long bone morphology of a diaphyseal bone. In certain variations, the primary bone plate has a configuration that may be complimentary to a planar portion of a bone portion, e.g., a diaphyseal bone portion, and in certain embodiments, the primary bone plate has a configuration that may be complimentary to a non-planar portion of a bone portion.

The primary bone plate may be configured for engaging or being associated with a bone plate extender and/or affixed or otherwise associated with a bone portion. For instance, a portion of the primary bone plate may be configured for being attached to or otherwise being associated with a portion of bone, e.g., a first bone portion, and another portion may be configured for being associated with or otherwise coupled to a bone plate extender and/or another portion of bone, e.g., a second bone portion. Specifically, a portion of the primary bone plate may include a configuration that allows the primary bone plate to be coupled with the bone plate extender described herein. Such a configuration may be any suitable configuration so long as it is capable of facilitating the association and/or coupling of the primary bone plate with the bone plate extender.

For instance, the primary bone plate may include one or more openings that are configured so as to allow the primary bone plate to be coupled with a bone plate extender. Specifically, one or both of the proximal and/or distal regions of the primary bone plate may include one or more openings, such as an opening that spans the thickness of the primary bone plate and extends between a bone contacting surface and a top surface thereof. For example, in certain embodiments, the primary bone plate includes an opening, wherein the opening may be configured so as to receive a fastener, such as a fastener that may be inserted through the opening and functions to couple the primary bone plate to one or more bone plate extenders.

Such an opening, as well as any other opening included in the bone plate system, may be of any suitable configuration, for instance, the opening may be round, e.g., circular or semi-circular, triangular, square, ovoid, arced, elliptical, or the like. For example, in certain embodiments, the opening may be circular and in certain embodiments the opening may be semi-circular, arced, or ovoid. In certain variations, two or more openings are included and positioned at the proximal portion of the primary bone plate. For instance, in certain embodiments, one or more openings are circular and an additional one or more openings may be semi-circular or arced or ovoid. Where an opening may be circular, it may have a diameter that ranges from about 0.5 mm to about 5 mm, such as from about 1 mm to about 4 mm, including about 2 mm or about 2.5 mm to about 3 mm. Where an opening may be ovoid, it may have a width that ranges from about 0.5 mm to about 5 mm, such as from about 1 mm to about 4 mm, including about 2 mm or about 2.5 mm to about 3 mm; and it may have a length that ranges from about 2 mm to about 15 mm, such as from about 5 mm to about 9 or about 10 mm, including about 7 mm to about 8 mm.

A suitable opening in the primary bone plate may be positioned anywhere along the length of the primary bone plate. In certain variations, a proximal, intercalating, or distal portion of the primary bone plate may be configured for being attached to a bone plate extender. Hence, in certain instances, the primary bone plate includes one or more openings, which openings are adapted so as to receive a fastener so as to attach the primary bone plate to a bone plate extender. Accordingly, in certain embodiments, the primary bone plate includes one or more, e.g., a plurality of openings, the configurations and dimensions of which are equivalent to those described above, wherein the openings are positioned in one or more of a proximal, intercalating and/or distal portion of the primary bone plate.

In certain variations, a proximal, intercalating, or distal portion of the primary bone plate may be configured for being attached to a bone portion. Hence, in certain embodiments, the primary bone plate includes one or more openings, which openings are adapted so as to receive a fastener so as to attach the bone plate to a bone portion. In certain embodiments, the openings are configured so as to receive a fastener, which fastener not only couples the primary bone plate with the bone plate extender but also joins the two bone plates to a portion of bone.

In certain embodiments, one or more openings, as described herein, include threading such as threading that corresponds to threading positioned on a fastener. In this manner, a fastener may be inserted into and through the opening by rotating the fastener in such a manner that the threads of the fastener align with the corresponding threads of the opening. In certain embodiments, one or more openings do not include threading such that the fastener may be inserted there through without threading the fastener into the opening.

As summarized above, in certain variations, the subject bone plate extension system includes a bone fixation element, such as a fastener. A bone fixation element of the subject disclosure may include an extended body. In certain variations, the extended body includes a proximal portion including a proximal end, a distal portion including a distal end, and an elongate portion extending between said proximal and distal portions.

In certain variations, the proximal portion includes a shaft, wherein the shaft includes at least one smooth region and at least one threaded region. In certain variations, the smooth region may be positioned between the proximal end and the threaded region and may include a length that corresponds to a thickness of a bone plate, e.g., a primary or extender bone plate.

In certain variations, the threaded region includes locking screw threads and may include a length that corresponds to a thickness of a bone plate, e.g., a primary or extender bone plate.

In certain variations, the proximal end may be configured for engaging a top surface of a bone plate. The elongate portion may or may not include threading and the distal portion may be conical in shape and tapered such that the distal end forms a point. Further, the fastener may include small projections or teeth that are configured for engaging the bone plate and/or extender, for instance, on each side. In certain embodiments, the fastener may include a smooth surface, and in certain embodiments, the surface may be knurled.

As summarized above, the bone plate system of the present disclosure may be employed to reduce and/or fix one or more bone portions for the treatment of a bone fracture, for example. Reference will now be made in detail to various embodiments of the disclosure, which are illustrated in the accompanying figures. Referring now to FIGS. 1-2, a bone plate extender of the present disclosure is provided.

As shown in FIGS. 1-2, the bone plate extender 1 is elongated and includes an extended body 10, which body includes a proximal portion 12, with a proximal end 14, a distal portion 16, with a distal end 18, and an intercalating portion 13, positioned between the proximal and distal portions, 14 and 16, respectively. The extended body 10 additionally includes a bottom surface 11 and a top surface 15.

The bone plate extender 1, further includes a bone plate engagement portion 20, positioned at a proximal end 14 of the extended body 10. The bone plate engagement portion 20 includes a bottom surface 21 and a top surface 25, such as a bottom surface that is configured for contacting and/or engaging a top surface of an additional bone plate, or a top surface that is configured for contacting and/or engaging a bottom or bone contacting surface of an additional bone plate. The bone plate engagement portion 20 further includes an opening 27 extending from the top 25 to the bottom 21 surface.

The bone plate extender 1, additionally includes a bone fixation portion 30, positioned at a distal end 18 of the extended body 10. The bone fixation portion 30 includes a bottom surface 31 and a top surface 35. The bone fixation portion 30 is adapted for being associated with a bone. Accordingly, the bone fixation portion 30 further includes an opening 37 extending from the top 35 to the bottom 31 surface.

As can be seen with reference to FIG. 1A, the bone plate extender 1 may be substantially planar. As such, the top surface 25 of the bone plate engagement portion 20, and the top surface 35 of the bone fixation portion 30, are coplanar with the top surface 15 of the extended body 10. Specifically, the top surface 15 of the extended body 10 corresponds to a primary plane 2 and both top surface 25 and top surface 35 are substantially in plane with primary plane 2.

Further, as depicted both the bone plate engagement portion 20 and the bone fixation portion 30 are configured as a single, circular element which element is planar and includes an opening there through, which opening is adapted for receiving at least a portion of a fixation element, e.g., a screw or peg, there through. As depicted, neither bone plate engagement portion 20 nor the bone fixation portion 30 includes threading, although it is understood that one or more of said portions could include threading such that the referenced openings would be configured for engaging a fixation element via such threads. Additionally, the thickness of the extended body 10 is substantially the same as the thickness of the bone plate engagement portion 20 and the bone fixation portion 30, such that top surfaces 15, 25, and 35 are substantially coextensive and/or coplanar with one another, e.g., are aligned in the same plane 2.

Figure 1B:
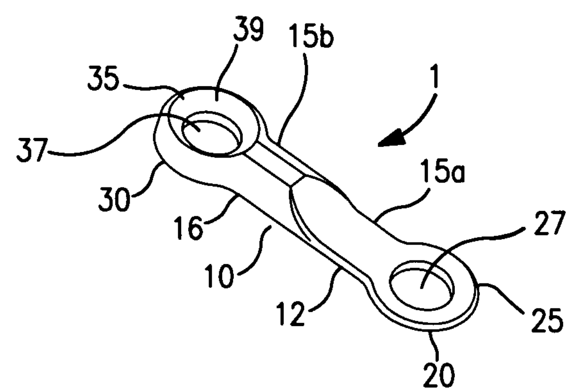
FIG. 1B depicts a bone plate extender, wherein the bone plate engagement portion includes a first thickness and the bone fixation portion includes a second thickness.

As can be seen with reference to FIG. 1B the bone plate extender 1 includes an extended body 10, which extended body includes a proximal portion 12 and a distal portion 16. As depicted the proximal portion 12 includes a first thickness and the distal portion 16 includes a second thickness, wherein the second thickness is greater than the first thickness. An intercalating portion is also included, wherein the thickness of the intercalating portion varies, for instance, it increases gradually from the proximal to the distal portion of the extended body. As can be seen, the top surface 15*a* of the proximal portion 12 of the elongate body 10 is not coextensive with the top surface 15*b* of the distal portion 16 of the elongate body 10. Rather, the proximal portion 12 and bone plate engagement portion 20 are flattened with respect to the distal portion 16 and the bone fixation portion 30.

For instance, as depicted, the bone plate engagement portion 20 is coextensive with the proximal portion 12 of the elongated body 10. Specifically, the top surface 25 of the bone plate engagement portion 20 is flush or otherwise aligned with the top surface 15*a* of the proximal portion 12 of the elongate body 10. Further, as can be seen, the distal portion 16 and bone fixation portion 30 are heightened with respect to the proximal portion 12 and the bone plate engagement portion 30.

For example, as depicted, the bone fixation portion 30 is coextensive with the distal portion 16 of the elongated body 10. Specifically, the top surface 35 of the bone fixation portion 30 is flush or otherwise aligned with the top surface 15*b* of the distal portion 16 of the elongate body 10. As depicted, the bone fixation portion 30 includes a recessed portion 39 surrounding opening 37, which recessed portion 39 is configured such that when a bone fixation element is received within the opening 37, a top surface of the bone fixation element is flush with or otherwise aligned with the top surface 35 of the bone fixation portion 30. It is to be noted that although the bone plate engagement portion 20 does not include a recessed portion surrounding opening 27, rather, top surface 25 is substantially planar, albeit including opening 27, in certain variations, the opening may be recessed.

As can be seen with reference to FIG. 1C, the bone plate extender 1 includes elongate body 10, bone plate engagement portion 20, and bone fixation portion 30. As depicted, bone plate engagement portion includes a plurality of openings 27*a* and 27*b*, while bone fixation portion 30 only includes one opening 37. It is to be noted that although the bone fixation element only includes a single opening, two, three, or more openings may be included therein.

As depicted, the bone plate engagement portion 20 includes a plurality of recessed portions 29*a* and 29*b* surrounding openings 27*a* and 27*b*, respectively, which recessed portions are configured such that if a bone fixation element (not shown) is received within the opening 27*a* and/or 27*b*, a top surface of the bone fixation element may be flush with or otherwise aligned with the top surface 25 of the bone fixation portion 20.

Further, as depicted, the bone fixation portion 30 includes a recessed portion 39 surrounding opening 37. The bone plate engagement portion 20 and the bone fixation portion 30 are coextensive with the proximal portion 12 of the elongated body 10. Specifically, the top surface 25 of the bone plate engagement portion 20 and the top surface 35 of the bone fixation portion are flush with or otherwise aligned with the top surface 15 of the proximal portion 12 of the elongate body 10.

FIG. 1D sets forth the bone plate extender 1 of FIG. 1C, however, as can be seen with reference to FIG. 1D, the bone plate engagement portion 20 is not coextensive with the elongate body 10 of the bone plate extender 1. Rather, the top surface 25 of the bone plate engagement portion 20 is offset from the top surface 15 of the elongate body 10 by a distance x, wherein distance x may be any suitable distance, but in some embodiments, distance x corresponds to the thickness of a bone plate, e.g., a primary bone plate as described herein. Specifically, although both top surface 25 and top surface 15 are planar they are not coplanar but offset, e.g., by a distance x, where x, in some embodiments, may be about 0.01 mm to about 5 mm, for instance, about 0.1 mm to about 2.5 mm, such as about 0.5 mm to about 1 mm. For instance, the elongate body 10 has a first thickness and the bone plate engagement portion 20 has a second thickness, wherein the first thickness is greater than the second thickness.

Due in part to this configuration, the bone plate engagement portion 20 of the bone plate extender 1 is adapted to fit underneath a bone plate, e.g., a primary bone plate, such that one or more of the openings 27*a* and 27*b* are aligned with one or more openings in the bone plate and, in some embodiments, the top surface 15 is flush with, e.g., coplanar with a top surface of the bone plate, e.g., primary bone plate, when the extender is properly associated therewith.

FIGS. 1E and 1F set forth additional configurations for the bone plate extender 1. As can be seen with reference to FIG. 1E, the bone plate engagement portion 20 is both flattened and extended. Additionally, the bone plate engagement portion 20 includes an oval or elliptical shape and thus, the opening 27 is configured as an oval. Further, the bone fixation portion 30 includes a plurality of openings 37*a* and 37*b*. The openings 37*a* and 37*b* serve a variety of functions, such as but not limited to, allowing the bone plate extender to attach to and/or grab a plurality of bone fragments, or to attach to and/or grab a plurality of different portions of the same bone fragment so as to provide increased fixation and support. Further, the presence of a plurality of openings allows one to choose the optimal fastener position, with respect to a bone fragment to be attached to the bone plate extender, by the insertion of a fastener through one of the plurality of openings. As depicted, top surfaces 35 and 15 are coplanar with one another, but not coplanar with top surface 25. Note, a portion of the proximal portion 12 of the elongate body 10 slopes down toward the bone plate engagement portion 20.

The bone plate extender 1 of FIG. 1F is similar to that of FIG. 1E, however, the bone plate engagement portion 20 includes a triangular shape and thus, the opening 27 is configured as a triangle. The oval and triangular openings may be configured so as to accommodate a plurality, e.g., 2, 3, or more screws therein, thus increasing the stability of the connection between the bone pate extender and a second bone plate, such as a primary bone plate.

Figure 1G:
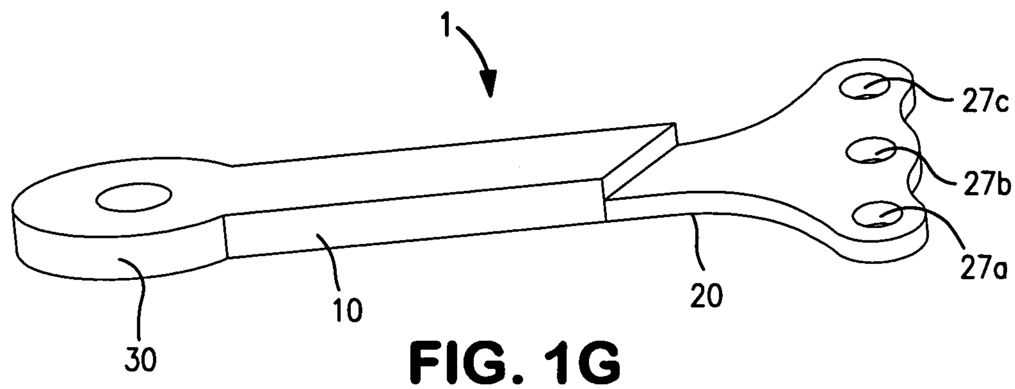
FIG. 1G depicts a bone plate extender, wherein the bone plate engagement portion includes a plurality of openings, e.g., three.

FIG. 1G sets forth an alternative configuration for the bone plate extender 1 of FIG. 1D, however, the bone plate engagement portion 20 of the bone plate extender 1 of FIG. 1G includes three openings 27*a*, 27*b*, and 27*c*. The multiple openings, e.g., 2, 3, 4, or more, of the bone plate engagement portion 20 allow the bone plate extender to be optimally positioned and secured to another, e.g., primary, bone plate. For instance, the multiple openings may used to adjust the angle and/or position of the bone plate extender relative to a primary plate to which the extender may be affixed. The bone plate engagement portion is not coplanar with the elongate body 10 and/or the bone fixation portion 30.

Figure 1H:
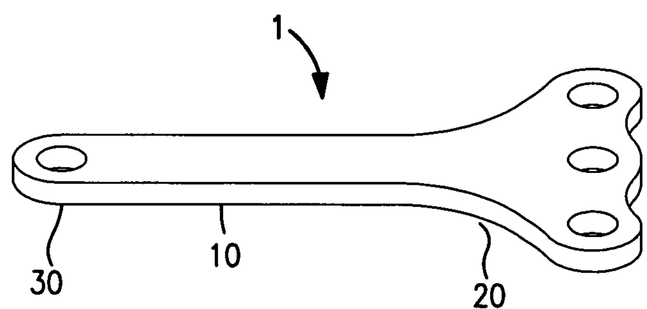
FIG. 1H depicts a planar bone plate extender, wherein the bone plate engagement portion includes a plurality of openings, e.g., three.

FIG. 1H sets forth an alternative configuration for the bone plate extender 1 of FIG. 1G, however, in FIG. 1H the bone plate engagement portion 20 is coplanar with the extended body 10 and the bone fixation portion 30, whereas in FIG. 1G the bone plate engagement portion 20 is not coplanar with the extended body 10 and the bone fixation portion 30.

Figure 1I:
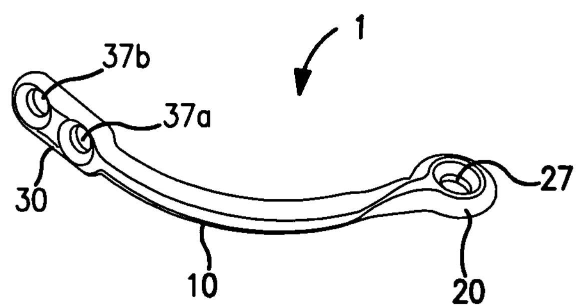
FIG. 1I depicts a non-planar bone plate extender wherein the extender body is arced or curved.

FIG. 1I sets forth another embodiment of the bone plate extender 1 of the subject disclosure. As can be seen with reference to FIG. 1I, the subject bone plate extender 1 is non-planar, curved, and includes an elongate body 10, a bone plate engagement portion 20, and a bone fixation portion 30. The bone plate engagement portion 20 is configured for engaging a bone plate, e.g., a primary bone plate and includes an opening 27. The bone fixation portion 30 is configured for receiving a bone fixation element and includes a plurality of openings 37*a* and 37*b*.

As depicted the elongate body 10 is both curved and twisted and thus in this manner the bone plate extender 1 is configured for both being attached to a primary bone plate via the bone plate engagement portion 20 and also for being associated with a bone portion, via the bone fixation portion 30, wherein the bone portion is distanced and out of plane from a primary bone plate to which the bone plate extender is to be attached. As described above in detail, in some embodiments, the degree of curvature of the elongate body may range from about 0 to about 90°, for instance, from about 15° to about 45°, such as from about 20° to about 30°.

Accordingly and as can be seen with reference to FIG. 2, the bone plate extender 1 may include one or more portions that are substantially non-planar. For instance, as depicted in FIG. 2A, the bottom surface 31 of the bone fixation portion 30 may be non-planar with respect to one or more of the bottom surface 11 of the elongate body 10, and/or the bottom surface 21 of the bone plate engagement element 20. Specifically, as illustrated, the bottom surface 31 is angled with respect to a primary plane 2, which primary plane comprises one or more of bottom surfaces 11 and 21.

Figure 2A:
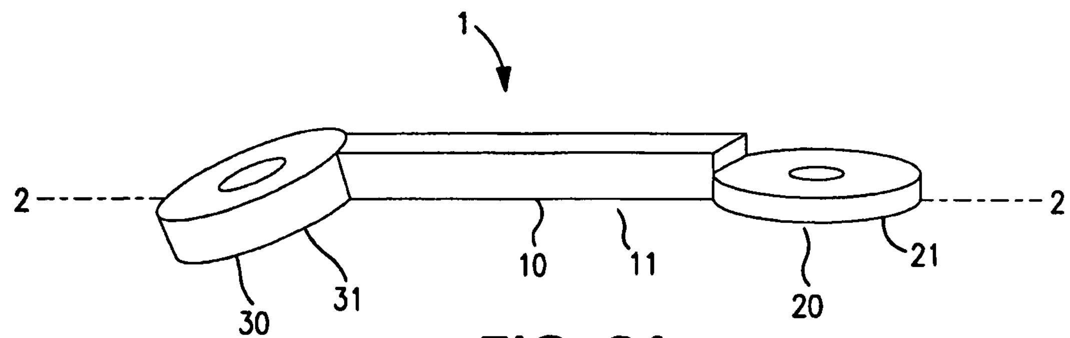
FIG. 2A depicts a non-planar bone plate extender, wherein the bone fixation portion is angled with respect to a plane defined by the bottom surface of the intercalating portion.
Figure 2B:
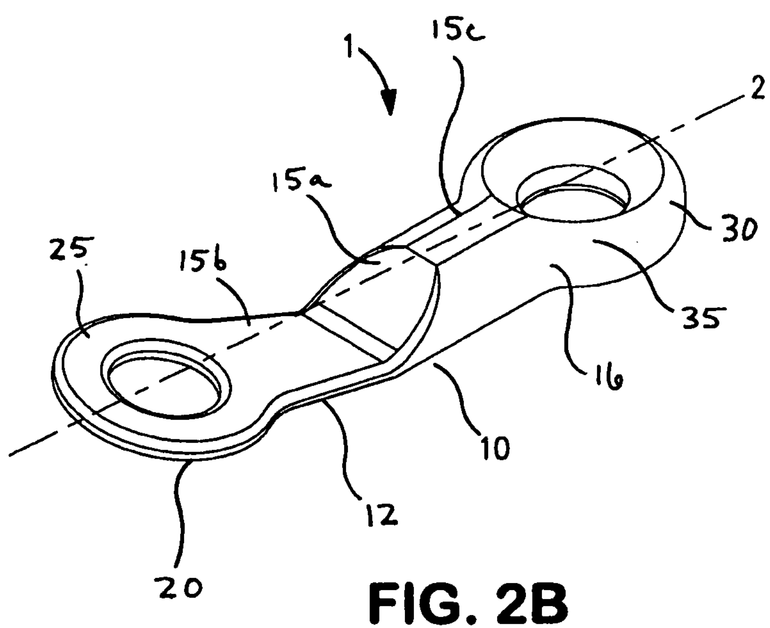
FIG. 2B depicts a non-planar bone plate extender, wherein the bone fixation portion is angled with respect to a plane defined by the top surface of the intercalating portion.

As depicted in FIG. 2B, top surface 25 of the bone plate engagement portion 20 and top surface 15*b* of portion 12 of the elongate body 10 may be non-planar with respect to one or more of the top surface 15*b* of the portion 16 and/or the top surface 35 of the bone plate engagement element 30. Specifically, as illustrated, top surfaces 35 and 15*a* are angled with respect to a primary plane 2, which primary plane comprises top surfaces 35 and 15*b*. It is to be noted that with respect to FIGS. 2A and 2B, although the bone fixation element is depicted as being angled with respect to one or more of a portion of the elongate body and/or the bone plate engagement portion, it is understood that the bone plate engagement portion may also be angled with respect to one or more of the elongate body and/or bone fixation portion.

Figure 2C:
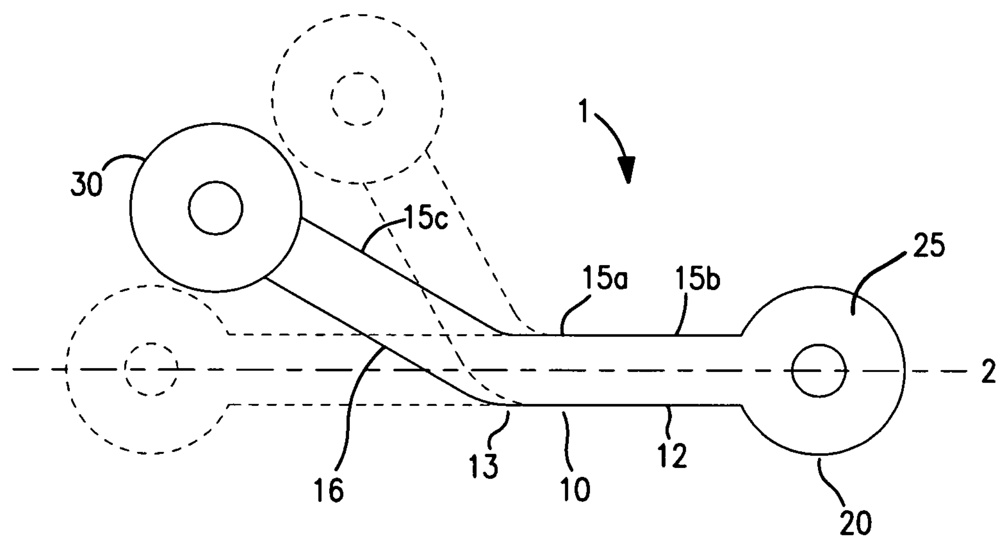
FIG. 2C depicts a bone plate extender, wherein a variety of angles between the bone plate engagement portion and the bone fixation portion are illustrated.

As depicted in FIGS. 2C-2F, one or more portions of the elongate body 10 may be angled or curved with respect to one or more other portions of the bone plate extender 1. For instance, as depicted in FIG. 2C, the distal portion 16 of the elongate body 10 may be angled with respect to the distal portion 12 and/or the bone plate engagement portion 20, wherein the angle may be from 0 to 90° or more. Specifically, a top surface 15*c* of the distal portion 16 may be angled with respect to a primary plane 2, which primary plane 2 corresponds to a top surface 15*a* and/or 15*b* and/or 25 of the bone plate extender 1.

Figure 2D:
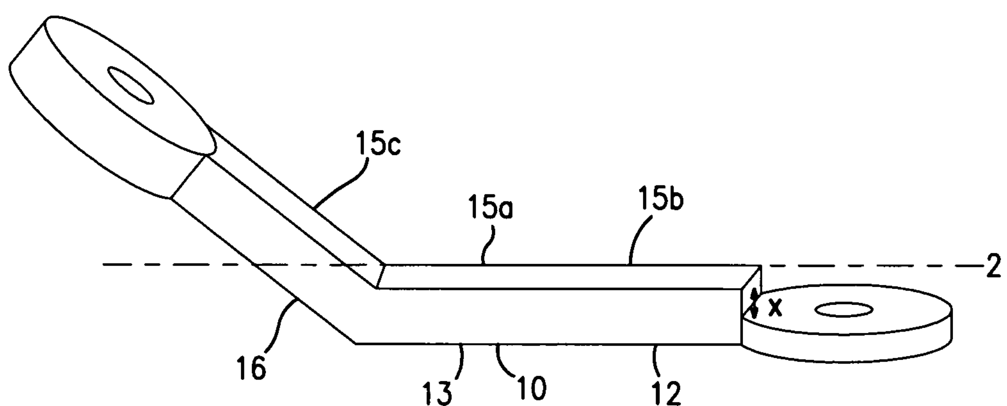
FIG. 2D depicts a non-planar bone plate extender, wherein the distal portion of the extended body is angled with respect to a plane defined by the top surface of the proximal portion of the extended body.

For instance, as can be seen with reference to FIG. 2D, top surface 15*c* of distal portion 16 may be angled with respect to plane 2 defined by the top surface 15*a* of intercalating portion 13 and top surface 15*b* of distal portion 12. Additionally, as depicted top surfaces 15*a* and 15*b* are not coplanar with top surface 25, but rather are offset there from, e.g., by a distance x.

Figure 2E:
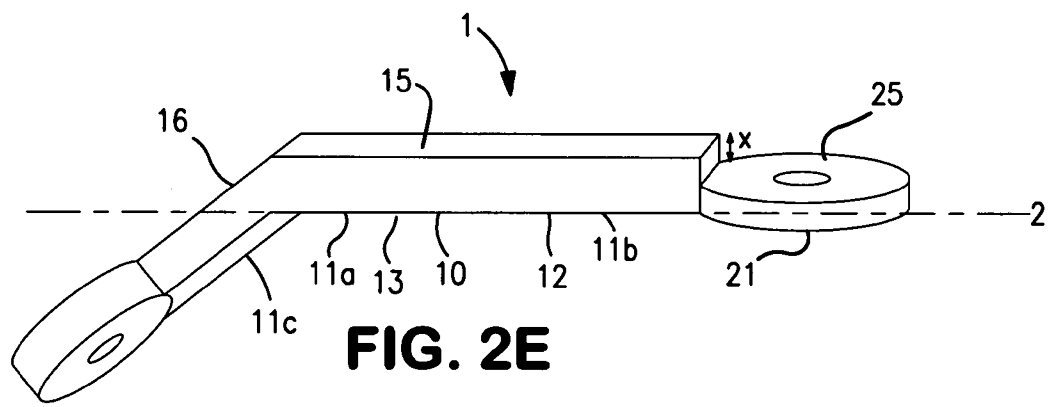
FIG. 2E depicts a non-planar bone plate extender, wherein the distal portion of the extended body is angled with respect to a plane defined by the bottom surface of the proximal portion of the extended body.

Further, as depicted in FIG. 2E, a primary plane 2 may correspond to bottom surface 11*a* of intercalating portion 13 and/or bottom surface 11*b* of proximal portion 12. Accordingly, bottom surface 11*c* of distal portion 16 may be angled with respect to plane 2 defined by the bottom surface 11*a* of intercalating portion 13 and bottom surface 11*b* of proximal portion 12. Additionally, as depicted top surface 15 is not coplanar with top surface 25, but rather are offset there from, e.g., by a distance x. Thus, as depicted in FIGS. 2C-2E, one or more portions of the bone plate extender may be angled with respect to one or more other portions thereof, wherein the angle may range from about 1° to about 90°, such as from about 5° to about 45°, for instance from about 7.5° to about 30°, including from about 10° to about 20°, such about as 15°.

Figure 2F:
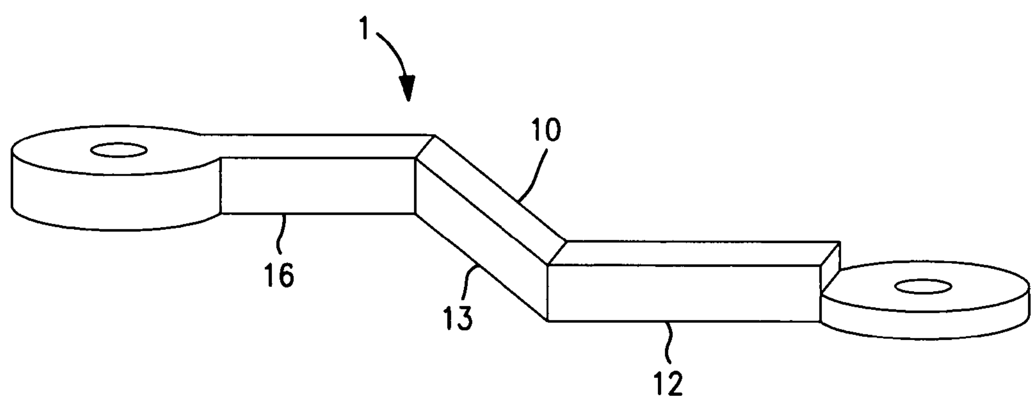
FIG. 2F depicts a bone plate extender, wherein the extended body includes a plurality of angles.

Further, as depicted in FIG. 2F, the bone plate extender may include one or a plurality of angels, e.g., internal angles. For instance, as depicted in FIG. 2F, the intercalating portion 13 of the elongate body 10 may be angled with respect to the proximal portion 12 and/or the distal portion 16 of the elongate body 10. It is to be noted that the bone plate extenders herein described could be provided pre-bent as described above or configured to be bent, e.g., during placement, so as to accommodate the shape of the bone and/or bone plate to which the extender is to be attached.

FIG. 3 depicts how the bone plate extender 1 of FIG. 1B may be associated with another bone plate, e.g., a primary bone plate 100. As can be seen with respect to FIG. 3A, at least the bone plate engagement portion 20 is configured for being associated with bone plate 100. Accordingly, in this regard, bone plate engagement portion 20 is planar and flattened with respect to raised elongate body 10 and bone fixation portion 30. Specifically, as can be seen with reference to FIG. 3B, top surface 25 of the bone plate engagement portion 20 is configured for contacting a bone contacting surface 111 of bone plate 100.

For example, bone plate engagement portion 20 may be slid underneath bone plate 100 or otherwise associated therewith in such a manner that opening 27 of bone plate engagement portion 20 aligns with an opening, such as openings 107*a*, 107*b*, or 107*c*, of bone plate 100. In this manner, bone plate extender 1 may be coupled to bone plate 100, e.g., by the insertion of a fixation element through openings 107 and 27. FIG. 3B provides a bottom view of the distal portion of the primary bone plate 100, showing the coupling of bone plate extender 1 with the bottom surface 111 of primary bone plate 100, such that top surface 25 of the bone plate extender contacts bottom surface 111 of the primary bone plate 100 such that openings 27 and 107*a* align. FIG. 3C provides a side view of the bone plate extender 1 and primary bone plate 100 of FIG. 3A, as depicted bone plate 100 is concave.

As can be seen with reference to FIG. 3, primary bone plate 100, may include an elongate element 110 and a transverse element 120, such that the bone plate 100 is in the shape of a "T". Further, as depicted, top surface 115 of elongate element 110 corresponds to a primary plane 101 and top surface 125 corresponds to a secondary plane 102, wherein primary plane 101 and secondary plane 102 are anti-parallel to one another, e.g., transect one another, such that an angle x is formed where angle x may range from about 1° to about 90°, such as from about 5° to about 45°, for instance from about 7.5° to about 30°, including from about 10° to about 20°, such about as 15°. Additionally, as depicted elongate body 110 is concave.

Figure 4A:
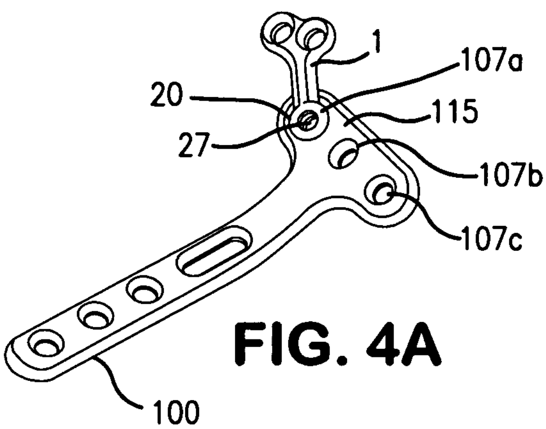
FIG. 4A depicts a perspective view of a bone plate extender appropriately aligned for coupling with a proximal portion of a primary bone plate.
Figure 4B:
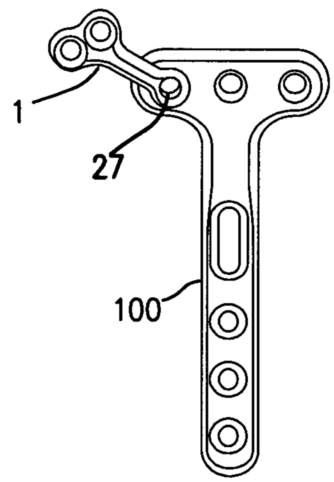
FIG. 4B depicts a front view of the bone plate extender and bone plate of FIG. 4A.
Figure 4C:
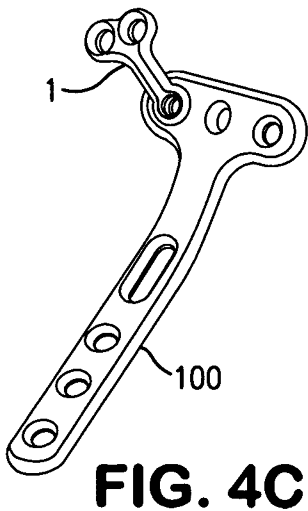
FIG. 4C depicts a slightly rotated view of the bone plate extender and bone plate of FIG. 4A, which view emphasizes the angled nature of the primary bone plate.

FIG. 4 depicts how the bone plate extender 1 of FIG. 1C may be associated with another bone plate, e.g., a primary bone plate 100. As can be seen with respect to FIG. 4A, at least a bone plate engagement portion 20 is configured for being associated with bone plate 100. Accordingly, in this regard, at least the bottom surface 21 (not shown) of the bone plate engagement portion 20 is planar and adapted for being associated with a top surface 115 of bone plate 100. For example, bone plate engagement portion 20 may be positioned on top of bone plate 100 or otherwise associated therewith in such a manner that opening 27 of bone plate engagement portion 20 aligns with an opening, such as opening 107*a*, 107*b*, or 107*c*, of bone plate 100. In this manner, bone plate extender 1 may be coupled to bone plate 100, e.g., and attached thereto by the insertion of a fixation element through openings 107 and 27. FIG. 4B provides a front view of the bone plate extender 1 in its association with primary bone plate 100 as shown in FIG. 4A. FIG. 4C provides a perspective view of the bone plate extender 1 in its association with primary bone plate 100 as shown in FIG. 4B.

Figure 5A:
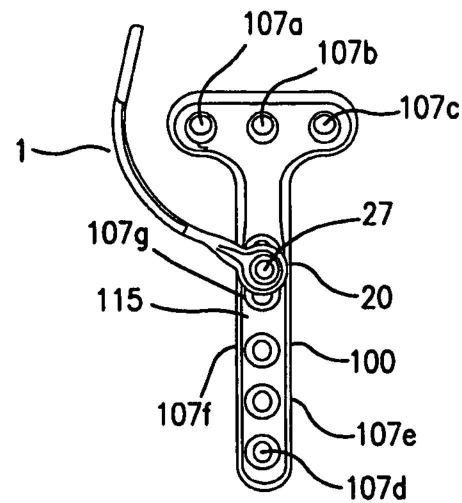
FIG. 5A depicts a front view of a bone plate extender appropriately aligned for coupling with a intercalating portion of a primary bone plate.

FIG. 5 depicts how the bone plate extender 1 of FIG. 1I may be associated with another bone plate, e.g., a primary bone plate 100. As can be seen with respect to FIG. 5A, at least a bone plate engagement portion 20 is configured for being associated with bone plate 100. Accordingly, in this regard, at least the bottom surface 21 (not shown) of the bone plate engagement portion 20 is planar and adapted for being associated with a top surface 115 of bone plate 100.

For example, bone plate engagement portion 20 may be positioned on a top surface of bone plate 100, or otherwise associated therewith, in such a manner that opening 27 of bone plate engagement portion 20 aligns with an opening, such as one of openings 107*a*, 107*b*, 107*c*, 107*d* 107*e*, 107*f*, 107*g*, etc. of bone plate 100. In this manner, bone plate extender 1 may be coupled to bone plate 100, and attached thereto e.g., by the insertion of a fixation element through openings 27 and 107.

As depicted, opening 27 is aligned with opening 107*g* of bone plate 100, which opening is elongated and configured as an oval. In this manner, bone pate extender 1 may be moved along opening 27*g* so as to achieve optimal alignment therewith. It is to be noted, that although the bone plate extender 1 is attached to a top surface of the bone plate 100, bone plate extender 1, could be configured for being coupled to a bottom surface of bone plate 100.

Figure 5B:
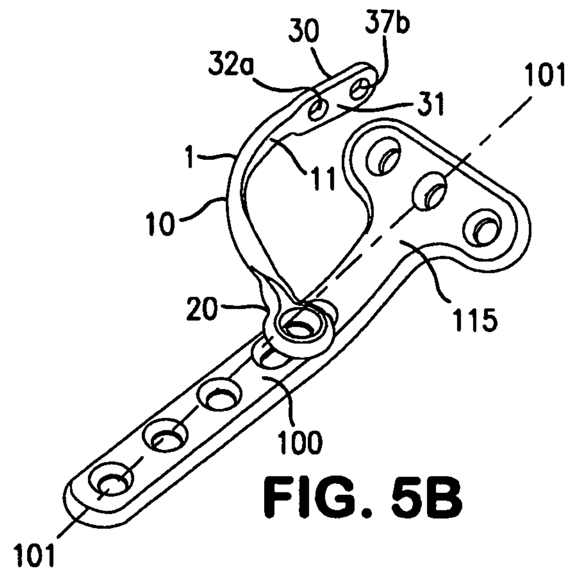
FIG. 5B depicts a perspective view of the bone plate extender and bone plate of FIG. 5B.

FIG. 5B provides a perspective view of the bone plate extender 1 and bone plate 100 of FIG. 5A. As can be seen with reference to FIG. 5B, the bone plate extender 1 is non-planar. Specifically, a bottom surface 11 of elongate body 10 of the bone plate extender 1 includes both a twist and an angled configuration with respect to the bottom surface 21 (not shown) of bone plate engagement portion 20 and the bottom surface 31 of bone fixation portion 30.

Thus, as depicted, the bone plate extender 1 may be associated with the primary bone plate 100 in such a manner that the elongate body 10 is extended, curved and out of plane with respect to the top surface 115 of the primary bone plate 100 and/or a primary plane 101 corresponding thereto. As depicted, bone fixation portion 30 includes a plurality of openings 37*a* and 37*b* through one or more of which a bone fixation element may be inserted so as to contact one or more bone portions in a manner sufficient to reduce the fractured bone portion in healing alignment with another bone portion, such as a bone portion contacted by primary bone plate 100. It is to be noted that the elongated, twisted, and/or curved configuration of elongate body 10 allows the bone plate extender 1 to contact a fractured bone portion that may be located distally and out of plane with respect to the bone plate 100 or a primary plane 101 corresponding to a top surface thereof.

Figure 5C:
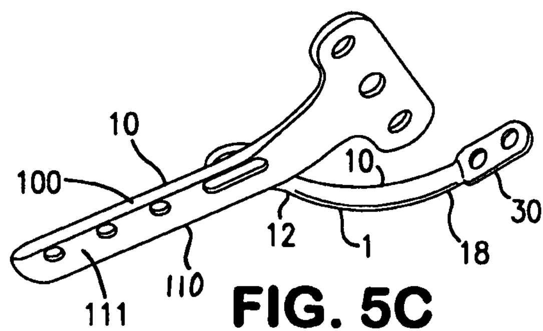
FIG. 5C depicts a bottom view of the bone plate extender and bone plate of FIG. 5A, which view emphasizes the curved, or concave nature of the primary bone plate.

FIG. 5C provides a reverse perspective view of the bone plate extender 1 and primary bone plate 100 of FIG. 5B. As can be seen with respect to FIG. 5C, the referenced twist is positioned along the proximal portion 12 of elongate body 10 and the referenced curve extends at least from proximal portion 12 to distal portion 16 and in this instance, continues through bone fixation portion 30. Further, as depicted, elongate body 110 of primary bone plate 100 includes a concave configuration, which concave configuration is adapted so as to allow the bottom surface 111 of elongate body 110 to conform to a specific bone morphology, such as a diaphyseal portion of a long bone, for example, a diaphyseal portion of a radius bone.

Figure 6A:
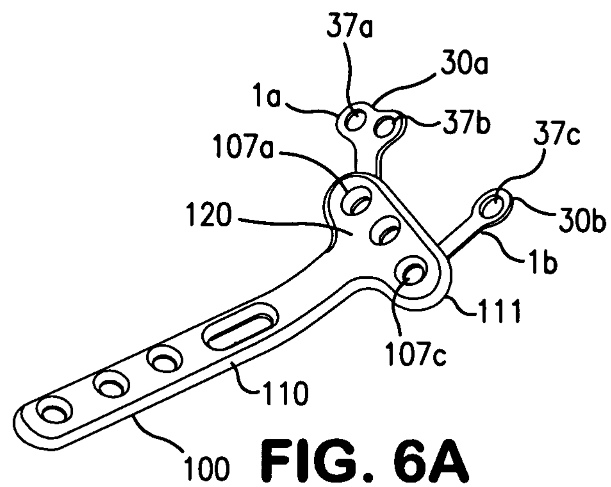
FIG. 6A depicts a perspective view of a primary bone plate having a plurality of bone plate extenders associated therewith, wherein the plurality of bone plate extenders includes the bone plate extender of FIG. 1A and the bone plate extender of 1C.

FIG. 6A depicts a primary bone plate 100 having one or a plurality of bone plate extenders 1*a* and/or 1*b* associated therewith. FIG. 6a illustrates that a plurality of bone plate extenders 1a and 1b may be configured for being associated with a bottom surface 111 of primary bone plate 100. As depicted, bone plate extender 1a is contacted with a transverse element 120 of bone plate 100 such that opening 27a (not shown) in bone plate extender 1a aligns with opening 107a in bone plate 100. Additionally, bone plate extender 1b is contacted with a different section of transverse element 120 of bone plate 100 such that opening 27b (not shown) in bone plate extender 1b aligns with opening 107c in bone plate 100.

As can be seen, bone fixation portion 30a of bone plate extender 1a includes a plurality of openings 37a and 37b, and bone fixation portion 20 of bone plate extender 1b includes a single opening 37c. Openings 37a, 37b, and 37c are configured for receiving a fixation element there through which fixation element(s) may contact one or more fractured bone portions that are positioned distally from primary bone plate 100 and in this manner the bone plate extenders 1a and 1b may reduce the contacted bone portions so as to be in healing alignment with another bone portion, such as a primary bone portion to which the primary bone plate 100 is associated.

Figure 6B:
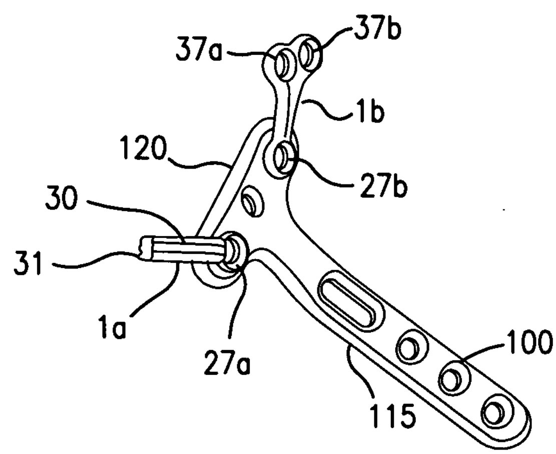
FIG. 6B depicts a perspective view of a primary bone plate having a plurality of bone plate extenders associated therewith, wherein the plurality of bone plate extenders includes the bone plate extender of FIG. 1C and a bone plate extender that includes a bent bone fixation portion that includes a plurality of hooks or teeth.

FIG. 6B illustrates that a plurality of bone plate extenders 1a and 1b may be configured for being associated with a top surface 115 of primary bone plate 100. As depicted, bone plate extender 1a is contacted with a top surface of transverse element 120 of bone plate 100 such that opening 27a in bone plate extender 1a aligns with opening 107a (not shown) in bone plate 100. Additionally, bone plate extender 1b is contacted with a different section of transverse element 120 of bone plate 100 such that opening 27b in bone plate extender 1b aligns with opening 107c (not shown) in bone plate 100.

As can be seen, bone fixation portion 30 of bone plate extender 1a does not include an opening, but rather is configured as a blade, which blade may be associated with a fractured bone portion so as to reduce the fractured bone portion in healing alignment, for instance, in alignment with a main bone portion, such as a bone portion to which primary bone plate 100 may be associated. Accordingly, the bone plate extender la includes a bent bone fixation portion that includes one or more teeth or hooks 31. Additionally, bone fixation portion 20 of bone plate extender 1b includes a plurality of opening 37a and 37b, one or more of which may be used to reduce and align an additional bone fracture portion or the same bone fracture portion as bone plate extender 1.

Figure 6C:
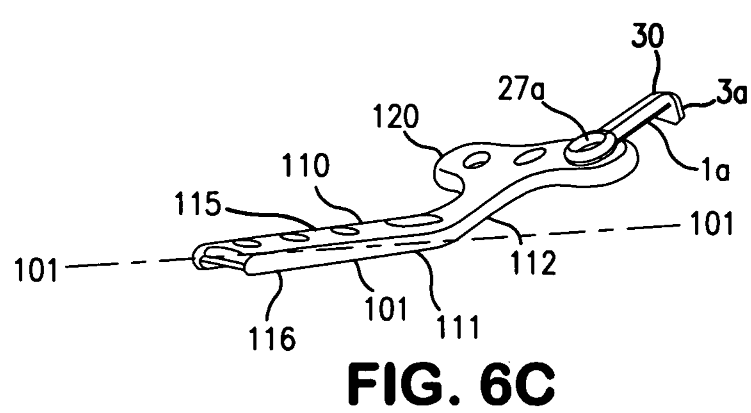
FIG. 6C depicts a perspective view of a primary bone plate having a single of bone plate extender associated therewith, wherein the bone plate extender includes a bent bone fixation portion that includes a plurality of hooks or teeth. It is to be noted, that as depicted, the bone plate extenders may be configured for being associated with a top surface of the primary bone plate or the bone plate extenders may be configured so as to be able to be associated with a bottom surface of the primary bone plate.

FIG. 6C presents a perspective view of bone plate extender 1 of FIG. 6B associated with bone plate 100 via the alignment of opening 27a in bone plate extender 1a and opening 107c (not shown) of bone plate 101. As can be seen with respect to FIG. 6C, a proximal portion 116 of elongate body 110 is angled with respect to the distal portion 112, such that the transverse section 120 is out of plane in relation to a primary plane 101 that corresponds to either a top 115 or bone contacting 111 surface of the elongate body 110, specifically, a proximal portion 116 thereof.

Figure 7:
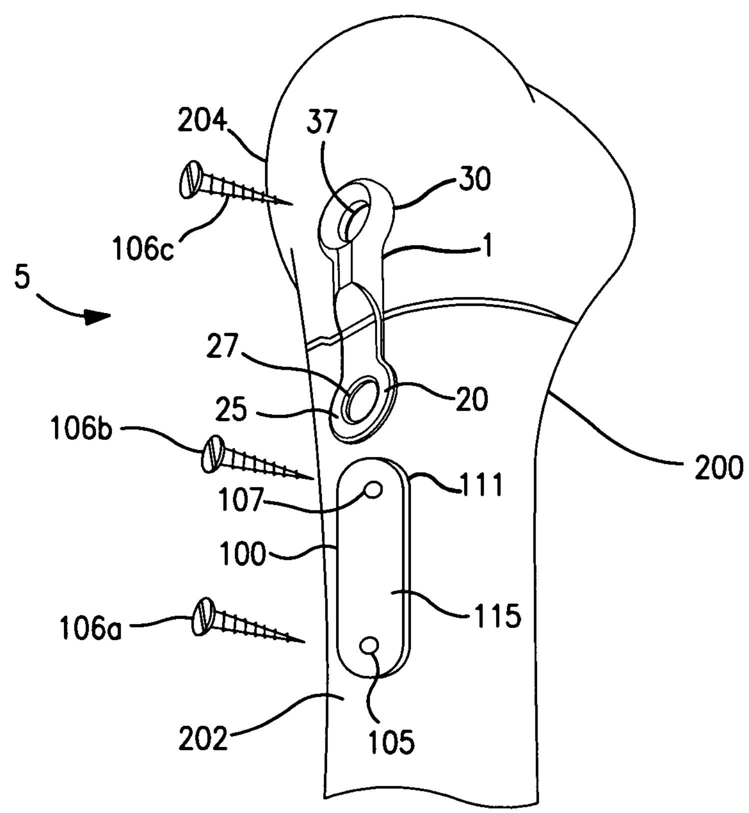
FIG. 7 depicts a bone plate system that includes a primary bone plate and the bone plate extender of FIG. 1B, which system may be applied to one or more bone portions so as to align, reduce, and/or stabilize a bone fracture.

FIG. 7 presents a bone plate system 5 which includes a primary bone plate 100 and a bone plate extender 1 (as illustrated in FIG. 1B), which system may be applied to one or more bone portions so as to align, reduce, and/or stabilize a bone fracture. For instance, as can be seen with reference to FIG. 7, a primary bone plate 100, such as a generic bone plate, may be positioned along a first bone portion 202, such as a long or diaphyseal bone portion, of a bone 200. For instance, as depicted, a primary bone plate 100 may be positioned on the radial side of a diaphyseal portion of the radius bone of the left arm. A fastener 106a may be inserted into opening 105 so as to attach the bone plate 100 to the first portion of bone 202.

Likewise, a bone plate extender 1 may be positioned along a second bone portion 204, such as a juxtaarticular or metaphyseal bone portion of the radial side of radius bone 200. As illustrated, the bone plate extender 1 includes a bone fixation portion 30 that includes an opening 37 for receiving a fastener 106c, which fastener may be inserted into opening 37 so as to attach the bone plate extender 1 to the second portion of bone 204.

Once the primary bone plate 100 and bone plate extender 1 have been appropriately positioned and attached to respective bone portions 202 and 204, the bone plate engagement portion 20 of the bone plate extender 1 may be slid or fitted underneath the primary bone plate 100 such that the top surface 25 comes into contact with the bone contacting surface 111 and openings 27 and 107 are aligned. It is to be noted, that although bone plate extender 1 is configured for being coupled with a bottom surface 111 of primary bone plate 100, in certain variations, a bone plate extender of the disclosure may be configured for being coupled to a primary bone plate via association with a top surface thereof. Once appropriately aligned the two bone plates may be coupled and attached to one another so as to reduce the two bone portions 202 and 204. Fastener 106b may then be inserted through openings 27 and 107c to attach the bone plates together and/or to the underlying bone 200 and thereby stabilize the fractured bone portions.

Figure 8A:
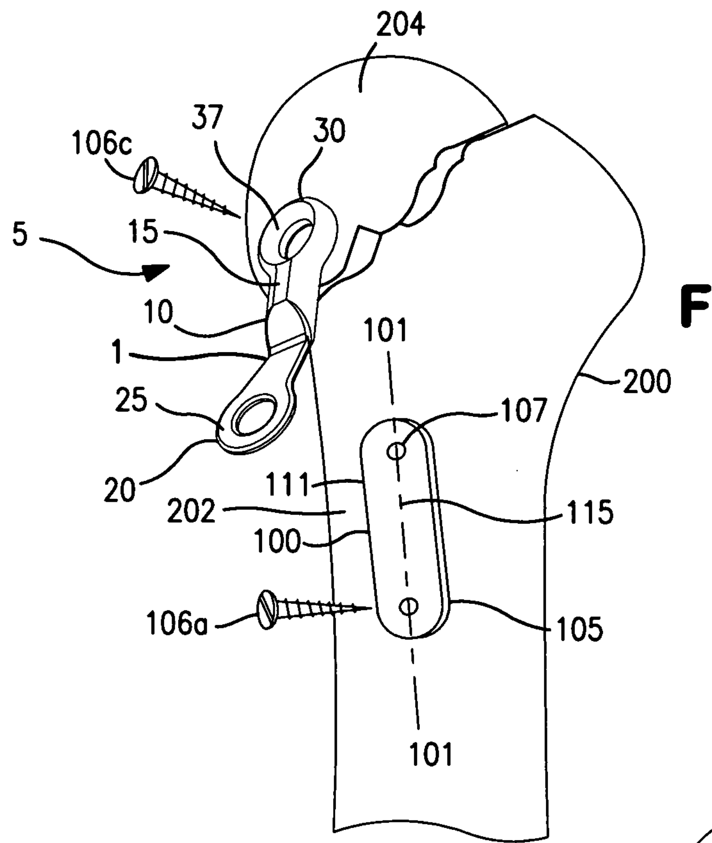
FIG. 8A depicts a bone plate extender affixed to a fractured and displaced bone portion as well as a primary bone plate affixed to a non-fractured bone portion, prior to reduction of the fractured bone portion.

FIG. 8 illustrates another embodiment of the bone plate system 5. As can be seen with respect to FIG. 8A, the bone plate system includes a generic primary bone plate 100. The primary bone plate 100 is planar, includes a top surface 115, a bone contacting surface 111, an opening 107 positioned in a distal portion of the bone plate, and an opening 105 positioned in a proximal portion of the bone plate. Top surface 115 corresponds to a primary plane 101. The primary bone plate 101 is positioned along a first bone portion shown here as the radial side of the distal radius, proximal to the fracture site 202, such as a long or diaphyseal bone portion of bone 200. Fastener 106a is inserted into opening 105 thereby attaching the bone plate 100 to the first portion of bone 202. As depicted in FIG. 8A, a distal, radial styloid portion 204 of a radius bone 200 is fractured and displaced with respect to a diaphyseal portion 202 of the radius bone 200.

As can be seen with reference to FIG. 8A, the bone plate system 5, also includes a bone plate extender 1, which bone plate extender is equivalent to the angled bone plate extender set forth in FIG. 2B. The bone plate extender 1 includes a bone plate engagement portion 20 that is non-planar with respect to the elongate body 10. Specifically, a top surface 25 of the proximal portion 20 is angled with respect to a top surface 15 of the elongate body 10. Thus, the bone plate engagement portion 20 is configured as a pre-bent member. As depicted, the bone fixation portion 30 of the bone plate extender 1 includes an opening 37 that is configured for receiving fastener 106c there through, which fastener passes through the opening and may be inserted into the bone portion 204.

Figure 8B:
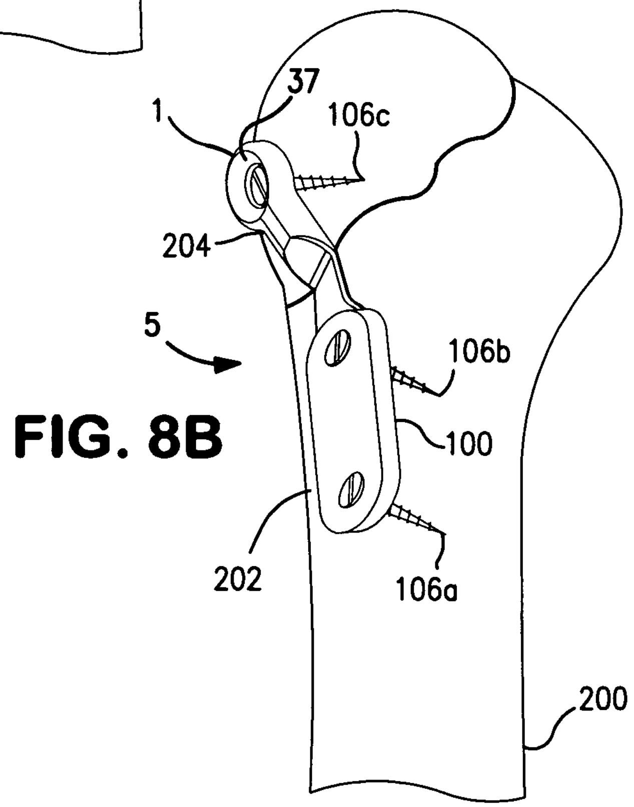
FIG. 8B depicts the bone plate extender and primary bone plate of FIG. 8A after reduction of the fractured portion.

With reference to FIG. 8B, the primary bone plate 100 is positioned and attached to bone portion 202 of radius bone 200 via fastener 106a. The bone plate extender 1 is positioned so as to contact and be attached to the fractured and displaced radial styloid portion 204 of radius bone 200. For instance, when properly aligned, fastener 106c may be at least partially inserted through recessed opening 37 so as to attach the bone plate extender 1 to the fractured radial styloid bone portion 204. The two plates may then be coupled together by sliding the bone plate engagement portion 20 of the bone plate extender 1 under bone plate 100 such that top surface 25 of the bone plate extender contacts bottom surface 111 of bone plate

100 and openings 27 and 107 align. A fastener 106*b* may then be inserted through the aligned openings. Specifically, once properly aligned and reduced, fastener 106*b* may be inserted through openings in the plates so as to join plates 1 and 100 and thereby stabilize the bone fracture.

Figure 9:
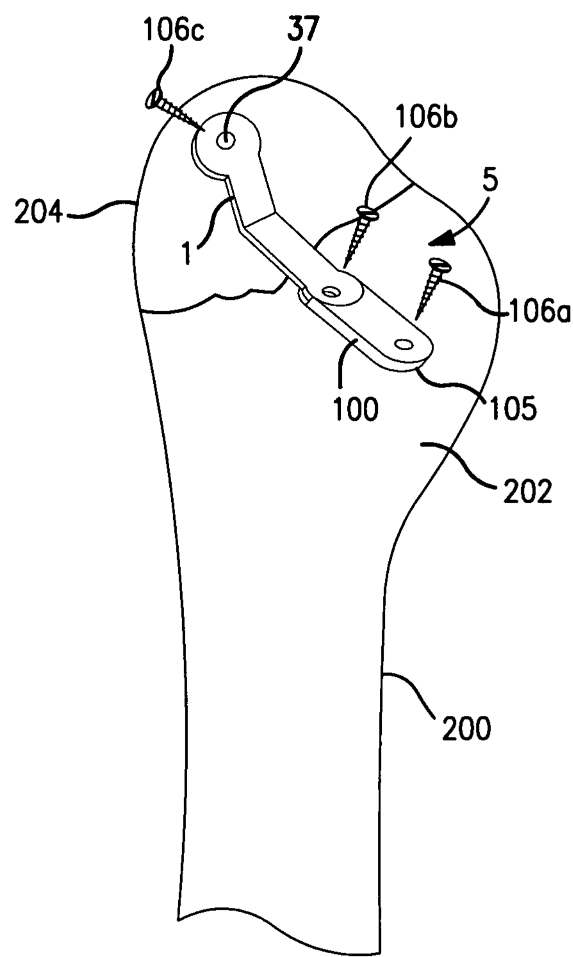
FIG. 9 depicts a bone plate system that includes a primary bone plate and the bone plate extender of FIG. 2E, which system may be applied to one or more bone portions so as to align, reduce, and/or stabilize a bone fracture.

As can be seen with reference to FIG. 9, the bone plate system 5 is applied so as to align, reduce, and/or stabilize a bone fracture. For instance, the primary bone plate 100 is positioned along a first bone portion 202, such as a long or diaphyseal bone portion of bone 200. The first bone plate 100 is positioned proximally and volarly on the distal radius and connects to the bone plate extender running distally and radially on the distal radius. Fastener 106*a* is inserted into opening 105 thereby attaching the bone plate 100 to the first portion of bone 202.

Likewise, the bone plate extender 1 (as illustrated in FIG. 2E) is positioned along a second bone portion 204, such as a juxtaarticular or metaphyseal bone portion of bone 200. As illustrated, the configuration of the bone plate extender 1 is adapted so as to model the morphology of the bone region to which the bone plate extender 1 is attached. For instance, the bone plate extender 1 is shaped to conform with the radial portion of the distal radius fixing to the radial styloid. Fastener 106*c* may be inserted into opening 37 so as to attach the bone plate extender 1 to the second portion of bone 204. The primary bone plate and bone plate extender may then be appropriately positioned and the openings 27 and 107 may be aligned and the bone plates coupled together and attached, e.g., via fastener 106*b*, so as to reduce the two bone portions 202 and 204 and thereby stabilize the fractured bone portions. As can be seen with reference to FIG. 9, the bone plate engagement portion of the bone plate extender 1 is configured for contacting and being coupled with a top surface of bone plate 100 for attachment thereto.

Figure 10A:
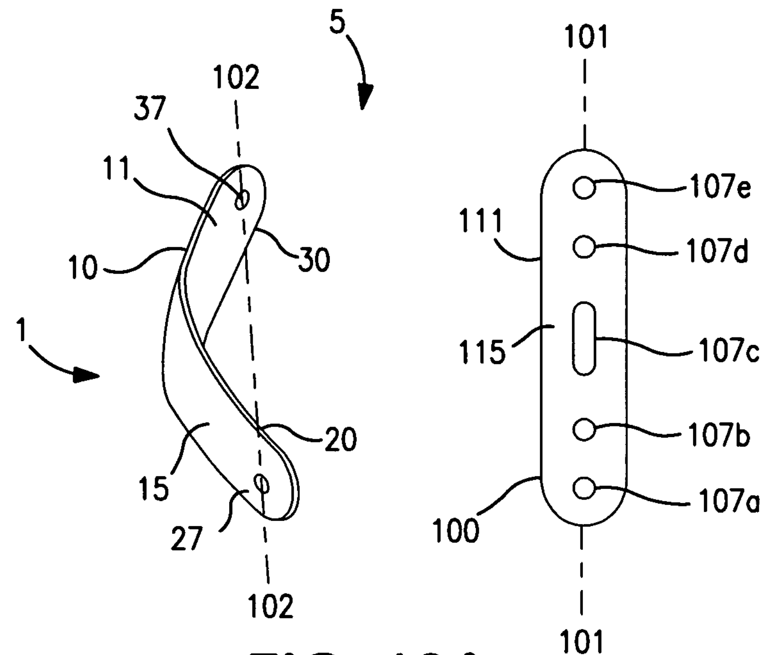
FIG. 10A depicts a system that includes a primary bone plate and a bone plate extender prior to association with respective bone portions.

FIG. 10 illustrates another variation of a bone plate system that includes the bone plate extender as depicted in FIG. 1I. As can be seen with respect to FIG. 10A, a bone plate system 5 is provided wherein the system includes a primary bone plate 100. The primary bone plate 100 is substantially planar and includes a top surface 115 with a plurality of openings 107*a*-107*e* extending there through to a bottom surface 111. The bottom surface 111 of the bone plate 100 defines a primary plane 101. The bone plate system 5, also includes a bone plate extender 1. The a bone plate extender 1 is non-planar and includes a top surface 15, a bone contacting surface 11, a bone plate engagement portion 20, which includes an opening 27, and additionally includes, a bone fixation portion 30 which includes an opening 37. A line transecting the aperture of openings 27 and 37 of the bone plate extender 1 defines a secondary plane 102.

Figure 10B:
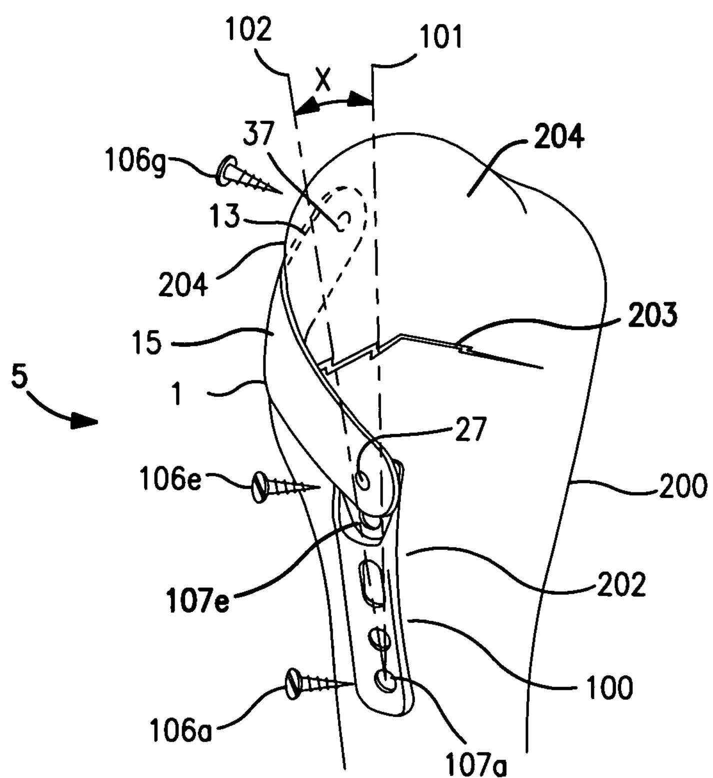
FIG. 10B depicts the bone plate system after having been applied to respective bone portions so as to align, reduce, and/or stabilize the bone fracture.

As illustrated in FIG. 10B, a distal, radial styloid portion 204 of a radius bone 200 is fractured and displaced with respect to a diaphyseal portion 202 of the bone 200. A primary bone plate 100 is positioned along the radial side of the distal radius, proximal to the fracture site 203 of the diaphyseal bone portion 202 of radius bone 200. Fastener 106*a* may be inserted into opening 107*a* thereby attaching the bone plate 100 to the first portion of bone 202. The bone plate extender 1 is positioned so as to contact and be attached to the fractured and displaced radial styloid portion 204. When properly aligned, fastener 106*g* may be inserted through opening 37 so as to attach the bone plate extender 1 to the fractured radial styloid bone portion 204. The two bone plates may then be coupled together by aligning the opening 27 of bone plate extender 1 with opening 107*e* of bone plate 100, so as to reduce the two bone portions 202 and 204 into an alignment that at least approximates the natural anatomical morphology of bone 200. Once properly aligned and reduced, fastener 106*e* may be inserted through openings in the plates so as to join plates 100 and 1 and thereby stabilize the bone fracture, as shown in FIG. 10B. As depicted, once the two bone plates are properly aligned and coupled together, primary plane 101 transects secondary plane 102 at an angle x.

Figure 10C:
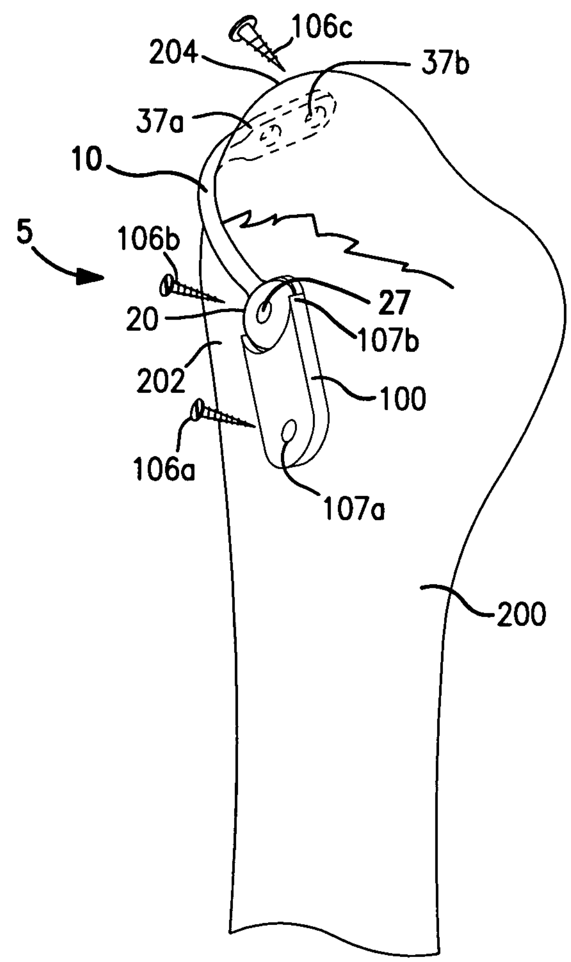
FIG. 10C depicts a bone plate system that includes a primary bone plate and the bone plate extender of FIG. 1I

As can be seen with reference to FIG. 10C, bone plate system 5 is applied so as to align, reduce, and/or stabilize a bone fracture. For instance, the primary bone plate 100 is positioned along a first bone portion 202, such as a long or diaphyseal bone portion of bone 200. For example, as depicted, the primary bone plate 100 is positioned along the proximal radial portion of the distal radius. Fastener 106*a* is inserted into opening 107*a* thereby attaching the bone plate 101 to the first portion of bone 202.

Likewise, the bone plate extender 1 (as illustrated in FIG. 1I) is positioned along a second bone portion 204, such as a juxtaarticular or metaphyseal bone portion of bone 200. For example, as depicted, the bone plate extender 1 is positioned distally to the primary plate 101 and wraps around the radial portion of the distal radius to the dorsal surface, attaching to a fractured portion of the distal radius or the distal radial styloid. As illustrated, the configuration of the bone plate extender 1 is adapted so as to model the morphology of the bone regions to which the bone plate extender is attached. Therefore, the elongate body 10 of the bone plate extender 1 includes a curved configuration.

A fastener 106*c* may be inserted into one of openings 37*a* or 37*b* so as to attach the bone plate extender 1 to the second portion of bone 204. The primary bone plate 100 and bone plate extender 1 may then be appropriately positioned and the openings 27 and 107 may be aligned. Fastener 106*b* may be inserted into and through openings 27 and 107 so as to couple the bone plates together to reduce the two bone portions 202 and 204 and thereby stabilize the fractured bone portions.

Figure 11A:
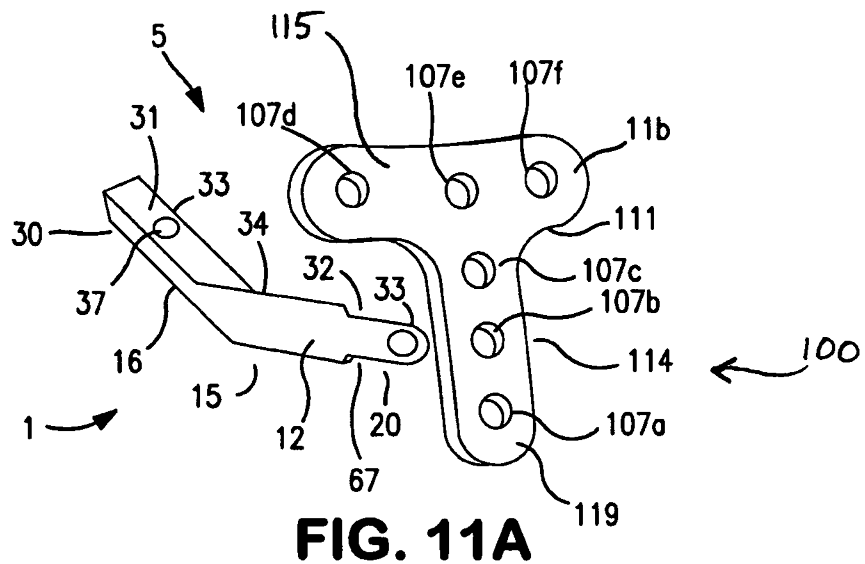
FIG. 11A provides a view of the bone plates prior to application to respective bone portions.

FIG. 11 illustrates another embodiment of a bone plate extender in conjunction with a bone plate system of the disclosure. As can be seen with respect to FIG. 11A, the bone plate system 5 includes a primary bone plate 100. The primary bone plate 100 is planar, includes a top surface 115 with a series of openings 107*a-f*, configured as openings. The primary bone plate 100 additionally includes a bone contacting surface 111. The top surface 115 defines a primary plane 101. As depicted the primary bone plate 100 includes a configuration in the shape of a "T." Specifically, the primary bone plate 100 includes a first section 114 and a second section 116, wherein the first section 114 bisects the second section 116, such that the primary bone plate 100 forms a "T" shape.

The bone plate system 5 of FIG. 1I further includes a bone plate extender 1. The bone plate extender 1 is non-planar and includes a proximal portion 12, with a proximal end 14, an intercalating portion 13, and a distal portion 16. The bone plate extender additionally includes a bone plate engagement portion 20, positioned at the proximal end 14, which bone plate engagement portion includes an opening 27. The bone plate engagement portion 20 is configured as an off-set tab member. For instance, as depicted, bone plate engagement portion 20 includes a ledge configuration 67 that is adapted so as to allow the engagement portion 20 to contact a top surface 115 of the primary bone plate 100 in order to be coupled therewith in a manner such that the bone contacting surface 11 of the bone plate extender 1 is aligned (e.g., flush) with the bone contacting surface 111 of the primary bone plate 100. The bone plate extender also includes a bone fixation portion 30 positioned at the distal portion 16, which bone fixation portion includes an opening 37. Bone plate extender 1 additionally includes a top surface 15 and an additional bone contacting surface 31. Additionally, as depicted, the bone plate extender 1 includes both a twist and an angled configuration such that the bone contacting surface 11 is twisted and out of plane with respect to the bone contacting surface 31 as illustrated by planes 102 and 103.

Figure 11B:
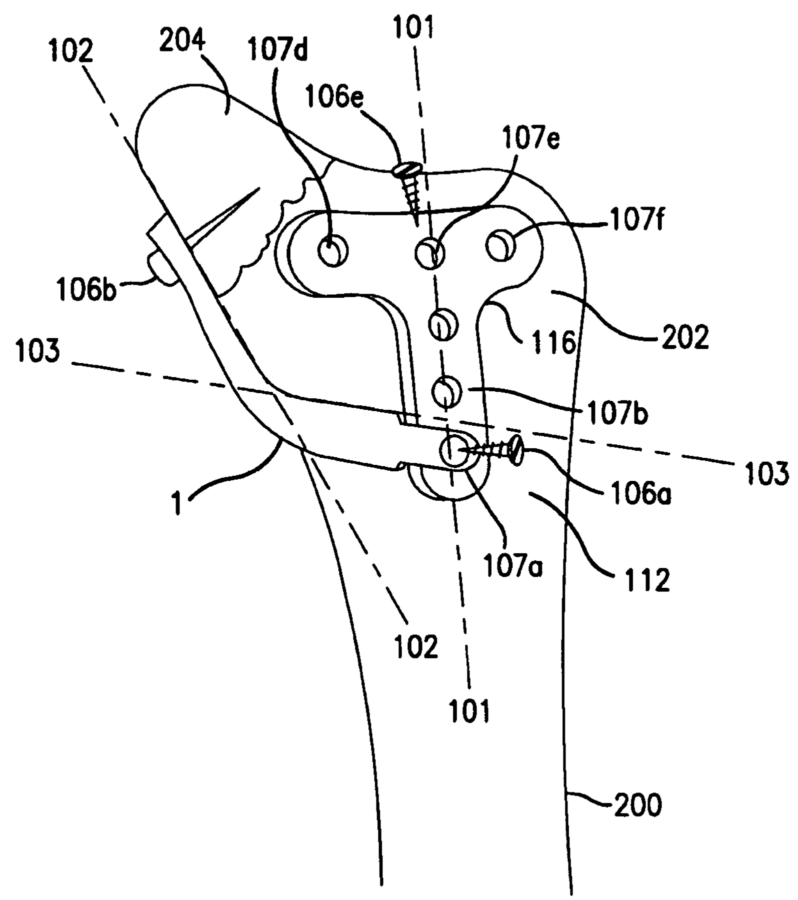
FIG. 11B shows the bone plates after they have been applied to respective bone portions.

As depicted in FIG. 11B, a distal, radial styloid portion 204 of a radius bone 200 is fractured. The primary bone plate 100 is positioned along a first bone portion 202, such as a long or diaphyseal bone portion of radius bone 200. Fastener 106*e* is inserted into opening 107*e* thereby attaching the bone plate 100 to a first portion of bone 202. The bone plate extender 1 is positioned so as to contact and reduce the fractured and displaced radial styloid portion 204 of radius bone 200. The bone plate extender 1 includes both a twist and a bend such that the bone plate extender 1 may wrap around one bone portion and contact a second bone portion such that the flat portion of the bone contacting surface 31 of the bone plate extender 1 contacts the second bone portion so as to align and reduce a fracture therein. For instance, the fractured portion of the radial styloid may be attached to the bone plate at it's most distal surface or in various locations along the radial surface of the distal radius radial styloid.

When the bone plate extender 1 is properly positioned, fastener 106*b* may be inserted through opening 37 so as to attach the bone plate extender 1 to the fractured radial styloid bone portion 204. The two bone plates may then be coupled together by aligning the tab member 20 of bone plate extender 1 with an opening 107*a-f* of bone plate 100 so as to reduce the two bone portions 202 and 204. Once properly aligned and reduced, a fastener, 106*a* may be inserted through the selected opening, e.g., 107*a*, so as to join plates 100 and 1 and thereby stabilize the bone fracture.

In one aspect, the disclosure is directed to a kit, wherein the kit includes a plurality of bone plates. In certain variations the kit includes one or more of a bone plate extender, a primary bone plate, and/or a fastener. For instance, in certain variations, the kit includes at least a primary bone plate and a bone plate extender, as described above, and may additionally include one or more fasteners. In certain variations the kit includes a plurality of bone plate extenders, a plurality of primary plates, and a plurality of fasteners. In certain variations the kit includes a plurality of bone plate extenders, as described herein below. For example, in certain variations, a kit is provided wherein the kit includes at least a plurality of bone plate extenders, such as a plurality of bone plate extenders described herein above. The bone plates, e.g., the bone plate extenders, and/or fasteners of the kit may be configured such that they may be bent, manipulated, mixed, matched, and attached to one or more bone portions and/or to each other so as to reduce, align, and stabilize a bone fracture through the use of a multiplicity of bone plates. The kit may also include suitable directions for using the components of the kit. Such as directions pertaining to mixing and matching the components. E.g., bone plate extender(s), so as to optimize usability.

Figure 12A:
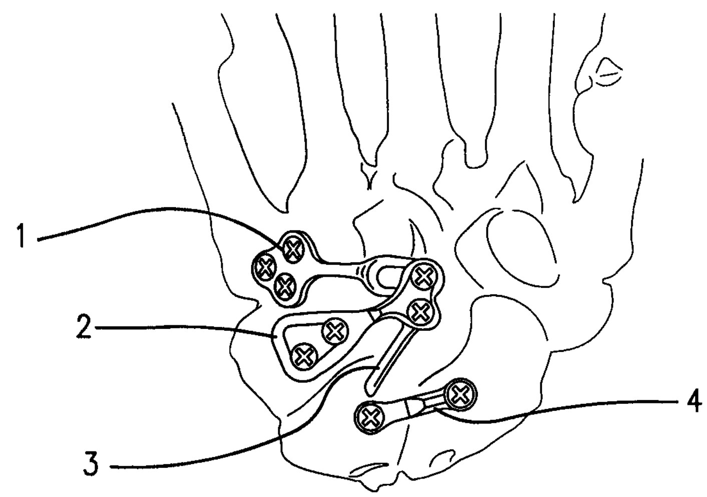
FIG. 12A, provides a bone plate system that includes a plurality of bone plate extenders, wherein the bone plate extenders have been applied to various bone portions of the hand.

Accordingly, FIG. 12 illustrates another embodiment of a bone plate system of the disclosure. For instance, in certain embodiments, a kit of bone plate extenders may be provided, wherein the kit includes a plurality of bone plate extenders, as described herein. In such an instance, the various bone plate extenders in the kit may be mixed, matched and coupled together so as to align, reduce, and stabilize a bone fracture, such as a comminuted bone fracture. As can be seen with respect to FIG. 12A, the bone plate system 5 comprises a kit that includes a plurality of bone plate extenders.

As depicted, bone plate extenders 1, 2, 3, and 4 are provided. Bone plate extender 1 is equivalent to the bone plate illustrated in FIG. 1H. Bone plate extender 2 is equivalent to the bone plate illustrated in FIG. 1F. Bone plate extender 3 is equivalent to the blade bone plate la illustrated in FIG. 6B. Bone plate extender 4 is equivalent to the bone plate illustrated in FIG. 1A. As can be seen with respect to FIG. 12B, the bone plate system 5 may further comprise a kit that includes the bone plate extender 5 illustrated in FIG. 1E as well as the bone extender 4 illustrated in FIG. 1A.

Figure 12B:
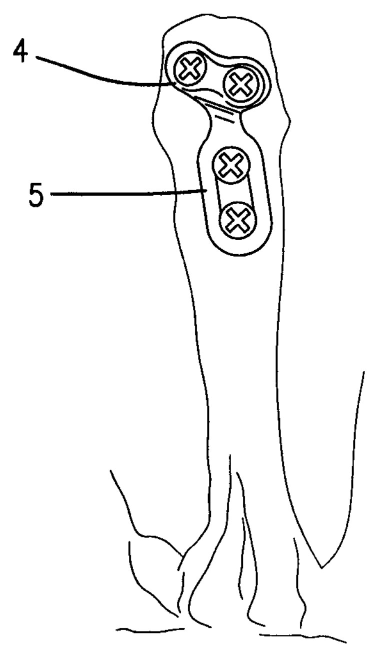
FIG. 12B, provides a bone plate system that includes a plurality of bone plate extenders, wherein the bone plate extenders have been applied to a bone portion of a finger.

The bone plate extenders of the kit are configured such that they can be bent, manipulated, mixed, matched, and attached to one or more bone portions and/or each other so as to reduce, align, and stabilize a bone fracture. As illustrated in FIG. 12A, the bone plate extender system may be used to reduce and stabilize a bone fracture such as a comminuted bone fracture involving one or more bones of the hand. And as illustrated in FIG. 12B, the bone plate extender system may be used to reduce and stabilize a bone fracture involving one or more bones of the fingers.

In one aspect, the subject matter described herein may be directed to methods of using such a bone plate extender and system, as described herein above, so as to align, reduce and/or fix one or more fractured bone portions for the treatment thereof, for example. Accordingly, in certain embodiments, a general method is provided for reducing a bone fracture, wherein the method includes the steps of providing a first bone plate, e.g., a primary bone plate, which bone plate may be any of a number of different bone plates well known and commercially available on the market or a bone plate extender of the subject disclosure, so long as the first bone plate includes at least an opening for receiving a fastener and may be configured for being attached to a bone portion, such as a diaphyseal portion of a long bone.

A bone plate extender such as that described above is also provided. As described above, the bone plate extender of the subject disclosure may be configured for being coupled to the first or primary bone plate. Once provided the first bone plate and bone plate extender may be attached to respective bone portions. For instance, the first bone plate may be attached to a first bone portion and the second bone plate may be attached to a second bone portion. Prior to or after attachment to respective bone portions the first bone plate and bone plate extender may be coupled together so as to reduce the fractured bone portions.

Accordingly, the primary bone plate and bone plate extender may be attached to their respective bone portions in any suitable order. For instance, the primary bone plate may be attached to a first bone portion prior to the attachment of the bone plate extender to a second bone portion or vice-verse. However, regardless of the order of the attachment of the primary bone plate and bone plate extender, the bone plate extender may be attached to a distal and/or fragmented bone portion and used as a lever so as to obtain correct anatomical alignment.

For example, the bone plate extender may be applied to a distal bone fragment. The application of the bone plate extender to the distal bone fragment may, but need not, involve the use of a K-wire which may be inserted through an opening in the bone plate extender, for instance, in the distal portion thereof, so as to be used as a guide to insure correct alignment of the bone plate extender to the distal fractured bone portion. Accordingly, the K-wire to be applied may be drilled parallel to an articular surface, such as in the lateral plane of the bone fragment. The bone plate extender may then be slid over the K-wire and down to the surface of the distal bone fragment. Once contacted and correctly positioned with respect to the distal bone fragment, the bone plate extender may be attached thereto by the insertion of one or more fasteners, e.g., pegs, through openings in the bone plate extender. K-wire may also be used to perform this function in addition or substitution for the referenced pegs.

If the primary bone plate has not heretofore been attached to the primary bone portion it may then be attached to its respective bone portion, for instance, in the manner described above with respect to the bone plate extender. Once the bone plate extender or both the primary bone plate and the bone plate extender are attached to their respective bone portions, the bone plate extender may be used, like a joystick, so as to align the two bone portions one with the other and/or align the bone plate engagement element of the bone plate extender with the primary bone plate in a manner sufficient to allow the primary bone plate and the bone plate extender to be coupled together.

It is to be noted that the bone plate extender is not only specifically designed, as described above, to conform to the morphology of the bone portion to which it is attached, but it is also designed such that when the bone plates are attached to their respective bone portions, the coupling of the primary bone plate with the bone plate extender results in the alignment and proper reduction of the respective bone portions such that when the primary bone plate and bone plate extender are attached to one another the fractured bone portions are stabilized in an alignment that approximates the normal anatomical alignment that the bone was in prior to the fracture and therefore promotes correct and rapid healing, with minimal adverse effects.

As certain changes may be made without departing from the scope of the present subject matter described herein, it is intended that all matter contained in the above description or shown in the accompanying drawings be interpreted as illustrative and not in a literal sense (and thus, not limiting). Practitioners of the art will realize that the method, device and system configurations depicted and described herein are examples of multiple possible system configurations that fall within the scope of the current subject matter described herein.

While the subject matter described herein has been described with reference to the specific embodiments thereof, it should be understood by those skilled in the art that various changes may be made and equivalents may be substituted without departing from the true spirit and scope of the subject matter described herein. In addition, many modifications may be made to adapt a particular situation, material, composition of matter, process, process step or steps, to the objective and scope of the subject matter described herein. All such modifications are intended to be within the scope of the claims appended hereto.

Throughout this application, various publications, patents and published patent applications may be cited. The disclosures of these publications, patents and published patent applications referenced in this application are hereby incorporated by reference in their entirety into the present disclosure. Citation herein by the Applicant of a publication, published patent application, or patent is not an admission by the Applicant of said publication, published patent application, or patent as prior art. Accordingly, all publications and patents cited in this specification are herein incorporated by reference as if each individual publication or patent were specifically and individually indicated to be incorporated by reference.

What is claimed is:

1. A bone plate extender, comprising an extended body, the extended body comprising:

a bone plate engagement portion comprising a bottom surface and a top surface, the bottom surface being substantially planar and configured for contacting a top surface of a bone plate;

a bone fixation portion adapted for being associated with a bone fixation element; and an intercalating portion extending between the bone plate engagement portion and the bone fixation portion and comprising a bottom surface and a top surface, the bone plate engagement portion and the bone fixation portion being twisted relative to one another about a centerline of the extended body.

2. The bone plate extender of claim 1, wherein a distance between the bottom and top surface of the bone plate engagement portion comprises a first thickness, and a distance between the bottom and top surface of the intercalating portion comprises a second thickness.

3. The bone plate extender of claim 2, wherein the first thickness and second thickness comprises a unitary thickness.

4. The bone plate extender of claim 1, wherein the intercalating portion is adapted so as to resist deformation.

5. The bone plate extender of claim 1, wherein the intercalating portion further comprises a proximal portion including a proximal end, a distal portion including a distal end, an intermediary portion positioned between the proximal and the distal portions, a top surface, a bottom surface opposite the top surface, and a primary plane, wherein the primary plane corresponds to either the top surface or the bottom surface.

6. The bone plate extender of claim 5, wherein the primary plane corresponds to the proximal portion, and the distal portion is out of plane with respect to the primary plane.

7. The bone plate extender of claim 6, wherein one of the top surface or the bottom surface comprises one or more secondary planes.

8. The bone plate extender of claim 6, wherein the distal portion is angled with respect to the proximal portion.

9. The bone plate extender of claim 6, wherein the bone fixation portion is angled with respect to the primary plane.

10. The bone plate extender of claim 1, wherein the bone fixation portion further comprises an opening extending between the top surface and a bone contacting surface, wherein the opening is configured for receiving a bone fixation element there through.

11. The bone plate extender of claim 10, wherein the bone fixation element comprises a fastener.

12. The bone plate extender of claim 1, wherein the bone plate engagement portion and the bone fixation portion are rotated relative to one another about the centerline to form a twist in the extended body.

13. The bone plate extender of claim 1, wherein the centerline of the extended body includes a spiral curve along a twist between the bone plate engagement portion and the bone fixation portion.

14. A bone plate extender, comprising an extended body, the extended body comprising:

a bone plate engagement portion comprising a bottom surface and a top surface, the bottom surface being substantially planar and configured for contacting a top surface of a bone plate;

a bone fixation portion adapted for being associated with a bone fixation element; and an intercalating portion extending between the bone plate engagement portion and the bone fixation portion and comprising a bottom surface and a top surface, the bone plate engagement portion and the bone fixation portion being twisted relative to one another about a centerline of the extended body, the bone plate engagement portion being bent along the centerline relative to the bone fixation portion.

15. The bone plate extender of claim 14, wherein the bone plate engagement portion and the bone fixation portion are rotated relative to one another about the centerline to form a twist in the extended body.

16. The bone plate extender of claim 14, wherein the centerline of the extended body includes a spiral curve along a twist between the bone plate engagement portion and the bone fixation portion.

* * * * *